(12) United States Patent
Lewis et al.

(10) Patent No.: US 8,242,103 B2
(45) Date of Patent: Aug. 14, 2012

(54) SULPHAMIDES FOR TREATMENT OF CANCER

(75) Inventors: Huw David Lewis, Sawbridgeworth (GB); Timothy Harrison, Belfast (GB); Mark Steven Shearman, Newton, MA (US)

(73) Assignee: Merck Sharp & Dohme Limited, Hertfordshire (GB)

( * ) Notice: Subject to any disclaimer, the term of this patent is extended or adjusted under 35 U.S.C. 154(b) by 816 days.

(21) Appl. No.: 11/920,450

(22) PCT Filed: May 16, 2006

(86) PCT No.: PCT/GB2006/050110
§ 371 (c)(1),
(2), (4) Date: Mar. 20, 2009

(87) PCT Pub. No.: WO2006/123185
PCT Pub. Date: Nov. 23, 2006

(65) Prior Publication Data
US 2009/0197904 A1  Aug. 6, 2009

(30) Foreign Application Priority Data
May 19, 2005 (GB) .................................. 0510213.2
Oct. 24, 2005 (GB) .................................. 0521562.9

(51) Int. Cl.
*A61K 31/553* (2006.01)
*A61K 31/535* (2006.01)
*A61K 31/435* (2006.01)
*A61K 31/445* (2006.01)
*A61K 31/44* (2006.01)

(52) U.S. Cl. ............ 514/211.09; 514/211.12; 514/232.8; 514/239.2; 514/295; 514/325; 514/340

(58) Field of Classification Search ............. 514/211.09, 514/211.12, 232.8, 239.2, 248, 295, 325, 514/340
See application file for complete search history.

(56) References Cited

FOREIGN PATENT DOCUMENTS

| WO | WO 02/36555 | 5/2002 |
|---|---|---|
| WO | WO 03/093251 | 11/2003 |
| WO | WO 03/093252 A1 | 11/2003 |
| WO | WO 03/093253 | 11/2003 |
| WO | WO 03/093264 | 11/2003 |
| WO | WO 2004/039800 | 5/2004 |
| WO | WO 2004/073630 | 9/2004 |
| WO | WO 2005/030731 | 4/2005 |
| WO | WO 2006/001956 | 1/2006 |

OTHER PUBLICATIONS

Calabresi and Chabner, Goodman & Gilman's The Pharmacological Basis of Therapeutics, 10th ed., 2001, p. 1388, para 2, lines 4-5.*
Vogelstein and Kinzler, The Genetic Basis of Human Cancer, 2nd ed., 2002, p. 3, col. 1, para 2.*
Weng, AP et al., Science, vol. 306, pp. 269-271 (2004), "Activating mutations of Notch 1 in human T cell acute lymphoblastic leukemia".
McKenzie, GJ et al., Expert Opinion on Therapeutic Targets, vol. 9(2), pp. 395-410 (2005), "Notch: a unique therapeutic target for immunomodulation".
Qin, JZ et al., Molecular Cancer Therapeutics, vol. 3(8), pp. 895-902 (2004), "p53-independent NOXA induction overcomes apoptotic resistance of malignant melanomas".
van Es, JH et al., Nature, vol. 435, pp. 959-963 (2005), "Notch/γ-secretase inhibition turns proliferative cells in intestinal crypts and adenomas into goblet cells".
Callahan, R et al., Journal of Mammary Gland Biology and Neoplasia, vol. 9(2), pp. 145-163 (2004), "Notch signaling in mammary development and oncogenesis".
Collins, BJ et al., Seminars in Cancer Biology, vol. 14, pp. 357-364 (2004), "Notch in lung development and lung cancer".
Axelson, H, Seminars in Cancer Biology, vol. 14, pp. 317-319 (2004), "Notch signaling and cancer: emerging complexity".
Zweidler-McKay, PA et al., Seminars in Cancer Biology, vol. 14, pp. 329-340 (2004), "Notch and T cell malignancy".
Weng, AP et al., Molecular and Cellular Biology, vol. 23(2), pp. 655-664 (2003), "Growth suppression of pre-T acute lymphoblastic leukemia cells by inhibition of notch signaling".
Allenspach, EJ et al., Cancer Biology & Therapy, vol. 1(5), pp. 466-476 (2002), "Notch signaling in cancer".
Curry, et al., Oncogen, vol. 24, pp. 6333-6344 (2005), "Gamma secretase inhibitor blocks Notch activation and induces apoptosis in Kaposi's sarcoma tumor cells".
Mealy, NE et al., Drugs of the Future, vol. 29(3), pp. 299-300, MPC-7869, 2004.
Tarassishin, L et al., PNAS, vol. 101(49), pp. 17050-17055, "Processing of Notch and amyloid precursor protein by γ-secretase in spatially distinct", 2004.

* cited by examiner

*Primary Examiner* — San-Ming Hui
(74) *Attorney, Agent, or Firm* — Joan E. Switzer; David A. Muthard

(57) ABSTRACT

Bridged bicyclic sulphamides of formula (I) are disclosed for treatment of cancer.

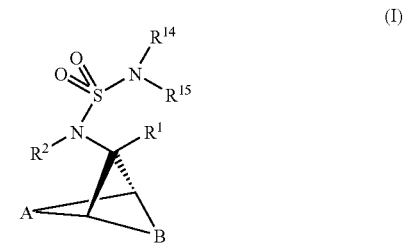

15 Claims, No Drawings

SULPHAMIDES FOR TREATMENT OF CANCER

PRIORITY CLAIM

This application is a §371 National Stage Application of PCT/GB2006/050110, filed on May 16, 2006, which claims priority from GB 0510213.2, filed on May 19, 2005 and GB 0521562.9, filed on Oct. 24, 2005.

This invention relates to methods and materials for treatment of the human or animal body. In particular it relates to the use of a particular class of sulphamides for treatment of cancer.

Notch signalling plays an important part in various cellular and developmental processes, including differentiation, proliferation, survival and apoptosis (Artavaris—Tsakonas et al, *Science* (1999), 284, 770-776). A significant body of evidence also indicates that augmented or abnormally-prolonged Notch signalling is involved in tumorigenesis (see, for example, Callahan and Egan, *J. Mammary Gland Biol. Neoplasia* (2004), 9, 145-163; Collins et al, *Semin. Cancer Biol.* (2004), 14, 357-64; Axelson, ibid. (2004), 14, 317-319; Zweidler-McKay and Pear, ibid (2004), 14, 329-340; and Weng et al, *Mol. Cell. Biol.* (2003), 23, 655-664).

Modified Notch1 signalling has been implicated in lymphoblastic leukemia/lymphomas, mammary gland tumors, lung cancer, neuroblastomas, skin cancer, cervical cancer, epithelial tumors and prostate cancer. (Allenspach et. al., *Cancer Biology and Therapy*, (2002) 1:5, 466-476).

Activating mutations in Notch1 are implicated in human T Cell Acute Lymphoblastic Leukemia (T-ALL) (Weng, et al., *Science*, 306:269-271 (2004)).

Notch signalling is elicited by receptor-ligand interaction between neighbouring cells. As a result of the receptor-ligand interaction, the Notch protein undergoes intra-membrane proteolysis, releasing an intracellular fragment which migrates to the nucleus where it modulates gene expression.

In view of the involvement in tumorigenesis, there has been much interest in inhibition of Notch signalling as a method of treating malignancies. Various types of intervention in the signalling process have been considered, such as inhibiting expression of the Notch protein, blockade of the receptor to prevent ligand binding, and inhibition of the intra-membrane proteolysis. The last-named is particularly attractive because the enzyme complex responsible for the proteolysis, gamma-secretase, has been extensively studied in connection with the cleavage of other protein substrates, notably amyloid precursor protein (APP) which is implicated in Alzheimer's disease. Hence a large number of compounds have been identified which can be shown to inhibit the cleavage of APP by gamma-secretase in vitro. The relevant compounds typically show equivalent ability to inhibit the cleavage of Notch protein by gamma-secretase in vitro (see Lewis et al *Biochemistry* (2003), 42, 7580-7586). However, clinical studies using such compounds have been severely hampered by the discovery of serious gastro-intestinal (GI) toxicity (believed to be mechanism based) associated with this class of compound (Searfoss et al, *J. Bio. Chem.* (2003), 278, 46107-46116; Wong et al, ibid (2004), 279, 12876-12882).

There is therefore a need for compounds which inhibit g-secretase and hence are suitable for use in treating disorders associated with Notch signalling activity, in particular cancer. Such compounds should preferably have pharmacokinetic, pharmacodynamic or other properties consistent with a therapeutic window allowing effective treatment of the relevant cancerous condition without incurring unacceptable side effects.

Therefore, in accordance with the invention there is provided the use, for the manufacture of a medicament for treating cancer, of a compound of formula I:

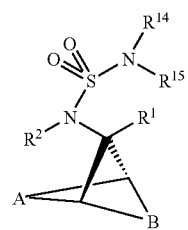

wherein:

A and B are independently selected from —(CXY)$_p$—; —(CXY)$_q$CY=CY(CXY)$_r$—; —(CXY)$_x$NR$^{13}$(CXY)$_y$—;

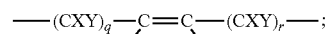
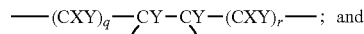
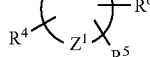
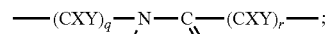
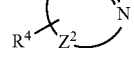

X represents halogen, R$^9$, —OR$^9$, —SR$^9$, —S(O)$_t$R$^{10}$ where t is 1 or 2, —OSO$_2$R$^9$, —N(R$^9$)$_2$, —COR$^9$, —CO$_2$R$^9$, —OCOR$^{10}$, —OCO$_2$R$^{10}$, —CON(R$^9$)$_2$, —SO$_2$N(R$^9$)$_2$, —OSO$_2$N(R$^9$)$_2$, —NR$^9$COR$^{10}$, —NR$^9$CO$_2$R$^{10}$ or —NR$^9$SO$_2$R$^{10}$;

Y represents H or C$_{1-6}$alkyl;

or X and Y together represent =O, =S, =N—OR$^{11}$ or =CHR$^{11}$;

provided neither A nor B comprises more than one —CXY— moiety which is other than —CH$_2$—;

Z completes an aromatic ring system of 5 to 10 atoms, of which 0 to 3 are selected from nitrogen, oxygen and sulfur and the remainder are carbon, or Z completes a non-aromatic ring system of 5 to 10 atoms, of which 0 to 3 are independently selected from oxygen, nitrogen and sulphur and the remainder are carbon;

Z$^1$ completes a non-aromatic ring system of 5 to 10 atoms, of which 0 to 3 are independently selected from oxygen, nitrogen and sulphur and the remainder are carbon;

Z$^2$ completes a 5- or 6-membered heteroaryl ring;

p is an integer from 1-6;

q and r are independently 0, 1 or 2;

x and y are independently 0, 1 or 2;

provided that at least one of A and B comprises a chain of 2 or more atoms, such that the ring completed by A and B contains at least 5 atoms;

R$^1$ represents H, C$_{1-4}$alkyl, or C$_{2-4}$alkenyl, or R$^1$ and R$^{15}$ together may complete a 5-, 6- or 7-membered cyclic sulfamide;

R$^2$ represents H, C$_{1-6}$alkyl, C$_{6-10}$aryl, C$_{6-10}$arylC$_{1-6}$alkyl, C$_{3-6}$cycloalkyl or C$_{2-6}$acyl which is optionally substituted with a carboxylic acid group or with an amino group;

$R^4$, $R^5$ and $R^6$ independently represent $R^9$, halogen, CN, $NO_2$, —$OR^9$, —$SR^9$, —$S(O)_tR^{10}$ where t is 1 or 2, —$N(R^9)_2$, —$COR^9$, —$CO_2R^9$, —$OCOR^{10}$, —CH=N—$OR^{11}$, —$CON(R^9)_2$, —$SO_2N(R^9)_2$, —$NR^9COR^{10}$, —$NR^9CO_2R^{10}$, —$NR^9SO_2R^{10}$, —CH=CHCH$_2$N(R$^{16}$)$_2$, —CH$_2$OR$^{10}$, —CH$_2$N(R$^{16}$)$_2$, —NHCOCH$_2$OR$^{10}$ or —NHCOCH$_2$N(R$^{16}$)$_2$;

$R^7$ represents H or $R^8$; or two $R^7$ groups together with a nitrogen atom to which they are mutually attached may complete a pyrrolidine, piperidine, piperazine or morpholine ring;

$R^8$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, Ar or —$C_{1-6}$alkylAr;

$R^9$ represents H or $R^{10}$; or two $R^9$ groups together with a nitrogen atom to which they are mutually attached may complete a pyrrolidine, piperidine, piperazine or morpholine ring which is optionally substituted by $R^{12}$, —$COR^{12}$ or —$SO_2R^{12}$;

$R^{10}$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, heterocyclyl, $C_{6-10}$aryl$C_{1-6}$alkyl, heteroaryl$C_{1-6}$alkyl, heterocyclyl$C_{1-6}$alkyl, $C_{6-10}$aryl$C_{2-6}$alkenyl, or heteroaryl$C_{2-6}$alkenyl, wherein the alkyl, cycloalkyl, alkenyl and alkynyl groups optionally bear one substituent selected from halogen, $CF_3$, $NO_2$, CN, —$OR^{11}$, —$SR^{11}$, —$SO_2R^{12}$, —$COR^{11}$, —$CO_2R^{11}$, —$CON(R^{11})_2$, —$OCOR^2$, —$N(R^{11})_2$ and —$NR^{11}COR^{12}$; and the aryl, heteroaryl and heterocyclic groups optionally bear up to 3 substituents independently selected from halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

$R^{11}$ represents H or $R^{12}$; or two $R^{11}$ groups together with a nitrogen atom to which they are mutually attached may complete a heterocyclic ring system of 3-10 atoms, 0-2 of which (in addition to said nitrogen atom) are selected from O, N and S, said ring system bearing 0-2 substituents selected from halogen, CN, $NO_2$, oxo, $R^{12}$, OH, $OR^{12}$, $NH_2$, $NHR^{12}$, CHO, $CO_2H$, $COR^{12}$ and $CO_2R^{12}$;

$R^{12}$ represents $C_{1-6}$alkyl which is optionally substituted with halogen, CN, OH, $C_{1-4}$alkoxy or $C_{1-4}$alkoxycarbonyl; perfluoro$C_{1-6}$alkyl, $C_{3-7}$cycloalkyl, $C_{2-6}$alkenyl, $C_{2-6}$alkynyl, Ar, —$C_{1-6}$alkylAr, ArO$C_{1-6}$alkyl or C-heterocyclyl which is optionally substituted with halogen, CN, $C_{1-6}$alkyl, OH, perfluoro$C_{1-6}$alkyl, $C_{2-6}$acyl, $C_{1-4}$alkoxy or $C_{1-4}$alkoxycarbonyl;

$R^{13}$ represents $R^9$, —$COR^{10}$, —$CO_2R^{10}$, —$SO_2R^{10}$, —$CON(R^9)_2$ or —$SO_2N(R^9)_2$;

$R^{14}$ represents H, $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, $C_{6-10}$aryl$C_{1-6}$alkyl, or heteroaryl$C_{1-6}$alkyl, wherein the alkyl, cycloalkyl, alkenyl and alkynyl groups optionally bear one substituent selected from halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$C_{1-6}$alkylNR$^7$COR$^8$, —$NR^7CO_2R^8$ and —$NR^7SO_2R^8$, and the aryl and heteroaryl groups optionally bear up to 3 substituents selected from $R^8$, halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$C_{1-6}$alkylNR$^7$COR$^8$, —$NR^7CO_2R^8$ and —$NR^7SO_2R^8$;

$R^{15}$ represents H or $C_{1-6}$alkyl; or $R^{15}$ and $R^1$ together complete a 5-, 6- or 7-membered cyclic sulfamide;

each $R^{16}$ independently represents H or $R^{10}$, or two $R^{16}$ groups together with the nitrogen to which they are mutually attached complete a mono- or bicyclic heterocyclic ring system of 5-10 ring atoms selected from C, N, O and S, said ring system optionally having an additional aryl or heteroaryl ring fused thereto, said heterocyclic system and optional fused ring bearing 0-3 substituents independently selected from halogen, oxo, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

Ar represents phenyl or heteroaryl either of which optionally bears up to 3 substituents independently selected from halogen, $CF_3$, $NO_2$, CN, $OCF_3$, $C_{1-6}$alkyl and $C_{1-6}$alkoxy;

"heterocyclyl" at every occurrence thereof means a cyclic or polycyclic system of up to 10 ring atoms selected from C, N, O and S, wherein none of the constituent rings is aromatic and wherein at least one ring atom is other than C; and "heteroaryl" at every occurrence thereof means a cyclic or polycyclic system of up to 10 ring atoms selected from C, N, O and S, wherein at least one of the constituent rings is aromatic and wherein at least one ring atom is other than C;

or a pharmaceutically acceptable salt thereof.

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl" $C_{1-6}$alkyl, "$C_{2-6}$alkynyl" and "$C_{1-6}$alkoxy" are to be construed in an analogous manner.

The expression "perfluoro$C_{1-6}$alkyl" as used herein refers to alkyl groups as defined above comprising at least one —$CF_2$— or —$CF_3$ group.

The expression "$C_{3-10}$cycloalkyl" as used herein refers to nonaromatic monocyclic or fused bicyclic hydrocarbon ring systems comprising from 3 to 10 ring atoms. Bicyclic systems comprising a nonaromatic hydrocarbon ring of 3-6 members which is fused to a benzene ring are also included. Examples include cyclopropyl, cyclobutyl, cyclopentyl, cyclohexyl, cyclohexenyl, decalinyl, tetralinyl and indanyl.

The expression "$C_{3-6}$cycloalkyl($C_{1-6}$)alkyl" as used herein includes cyclopropylmethyl, cyclobutylmethyl, cyclopentylmethyl and cyclohexylmethyl.

The expression "$C_{2-6}$acyl" as used herein refers to ($C_{1-5}$ alkyl)carbonyl groups, such as acetyl, propanoyl and butanoyl, including cycloalkyl derivatives such as cyclopentanecarbonyl and cyclobutanecarbonyl.

$C_{6-10}$aryl groups include phenyl and naphthyl, preferably phenyl.

The expression "$C_{6-10}$aryl$C_{1-6}$alkyl," as used herein includes benzyl, phenylethyl, phenylpropyl and naphthylmethyl.

The expression "heterocyclyl" as used herein means a cyclic or polycyclic system of up to 10 ring atoms selected from C, N, O and S, wherein at least one ring atom is other than carbon and said atom is part of a non-aromatic ring. Preferably not more than 3 ring atoms are other than carbon. Suitable heterocyclyl groups include azetidinyl, pyrrolidinyl, terahydrofuryl, piperidinyl, piperazinyl, morpholinyl, thiomorpholinyl, tetrahydropyranyl, tetrahydropyridinyl, imidazolinyl, dioxanyl, benzodioxanyl and 5-aza-2-oxabicyclo [2.2.1]heptyl. Unless indicated otherwise, attachment of heterocyclyl groups may be through a carbon or nitrogen atom forming part of the heterocyclic ring. "C-heterocyclyl" indicates bonding through carbon, while "N-heterocyclyl" indicates bonding through nitrogen.

The expression "heteroaryl" as used herein means a cyclic or polycyclic system of up to 10 ring atoms selected from C, N, O and S, wherein at least one of the constituent rings is aromatic and comprises at least one ring atom which is other than carbon. Preferably not more than 3 ring atoms are other than carbon. Where a heteroaryl ring comprises two or more atoms which are not carbon, not more than one of said atoms may be other than nitrogen. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of suitable heteroaryl ring systems include 1,2,4-triazine and 1,3,5-triazine The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Regardless of the presence or absence of asymmetric centres, certain compounds in accordance with the invention exist as enantiomers by virtue of the asymmetry of the molecule as a whole. For example, the compounds of formula I in which A comprises a monosubstituted fused benzene ring lack a plane of symmetry, and hence exist as pairs of enantiomers, the interconversion of which is prevented by the rigidity of the bridged bicycloalkyl ring structure. It is to be understood that all such isomers and mixtures thereof in any proportion are encompassed within the scope of the present invention, and that structural formulae depicting asymmetric molecules of this type shall be representative of both of the possible enantiomers, unless otherwise indicated.

The compounds of formula I are sulfamido-substituted bridged bicycloalkyl derivatives, optionally comprising a further fused ring system. In some embodiments, the sulfamide group forms part of a spiro-linked ring of 5, 6 or 7 members.

In the definition of A and B in formula I,
p is an integer from 1 to 6, preferably from 2 to 5, and most preferably is 3 or 4;
q and r are independently 0, 1 or 2 but are preferably both 1 or both 0;
and x and y are independently 0, 1 or 2, but are preferably not both 0;
with the proviso that at least one of A and B must comprise a chain of 2 or more atoms, such that the ring completed by A and B contains at least 5 atoms. Thus, for example, if A and B represent —(CXY)$_p$— and —(CXY)$_x$—NR$^{13}$—(CXY)$_y$— respectively, then p must be greater than 1 or at least one of x and y must be greater than 0.

X represents halogen, R$^9$, —OR$^9$, —SR$^9$, —S(O)$_t$R$^{10}$ where t is 1 or 2, —OSO$_2$R$^9$, —N(R$^9$)$_2$, —COR$^9$, —CO$_2$R$^9$, —OCOR$^{10}$, —OCO$_2$R$^{10}$, —CON(R$^9$)$_2$, —SO$_2$N(R$^9$)$_2$, —OSO$_2$N(R$^9$)$_2$, —NR$^9$COR$^{10}$, —NR$^9$CO$_2$R$^{10}$ or —NR$^9$SO$_2$R$^{10}$; wherein R$^9$ and R$^{10}$ are as defined above. Alternatively, X and Y together may represent =O, =S, =N—OR$^{11}$ or =CHR$^{11}$. Typically, X represents H, C$_{1-4}$alkyl, substituted C$_{1-4}$alkyl, —OR$^{9a}$, —COR$^{9a}$, —CO$_2$R$^{9a}$, —OCOR$^{9a}$, =N(R$^{9a}$)$_2$, —CON(R$^{9a}$)$_2$, —OCO$_2$R$^{10a}$, —OSO$_2$R$^{10a}$ or (in combination with Y)=O, =S, =N—OR$^{11}$ or =CH$_2$, where R$^{9a}$ is H or R$^{9a}$, and R$^{10a}$ is C$_{1-6}$alkyl, C$_{2-6}$alkenyl, Ar (especially phenyl) or benzyl. Preferred embodiments of X include H, methyl, hydroxymethyl, —CO$_2$Et, and (in combination with Y)=O, =S, =N—OMe, =N—OEt, =N—OPh, =N—OCH$_2$Ph and =CH$_2$.

Y may represent H or C$_{1-6}$alkyl, or may combine with X as indicated above. Preferably, Y represents H or together with X represents =O, =S, =N—OMe, =N—OEt, =N—OPh, =N—OCH$_2$Ph or =CH$_2$.

Neither A nor B may comprise more than one —CXY— moiety which is other than —CH$_2$—.

When A and/or B comprises a —NR$^{13}$— moiety, R$^{13}$ preferably represents H, optionally-substituted C$_{1-6}$alkyl, C$_{2-6}$alkenyl or C$_{6-10}$arylC$_{1-6}$alkyl. Particular values for R$^{13}$ include H, methyl, ethyl, allyl, cyanomethyl, carbamoylmethyl, methoxycarbonylmethyl, benzyl, chlorobenzyl and methoxybenzyl. Preferably, A and B do not both comprise a —NR$^{13}$— moiety.

Suitable embodiments of A and B include:
—CXY—, —CH$_2$CXY—, —CH$_2$CXYCH$_2$—, —CH$_2$CH$_2$CXYCH$_2$—, —CH=CH—, —CH$_2$CH=CHCXY—, —CH$_2$NR$^{13}$CXY—, —CH$_2$CH$_2$NR$^{13}$CXY—, —CH$_2$CXYNR$^{13}$CH$_2$—, —CXYCH$_2$NR$^{13}$CH$_2$—, —NR$^{13}$CXY—,

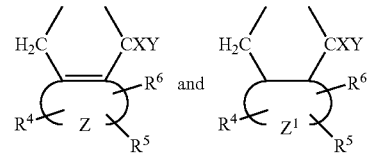

Preferred embodiments of A include —CH$_2$CH$_2$CH$_2$—, —CH$_2$CH$_2$—, —CH$_2$CH$_2$CH$_2$CH$_2$—, —CH$_2$CH=CHCH$_2$—, and

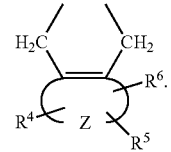

Typical embodiments of B include —CH$_2$—, —CH$_2$CH$_2$—, —CH$_2$CH$_2$CH$_2$—, —CH$_2$CH$_2$CH$_2$CH$_2$—, —CH=CH—, and —CH$_2$CH=CHCH$_2$—, and preferred embodiments of B include —CH$_2$CH$_2$— and —CH$_2$CH$_2$CH$_2$—.

Z completes an aromatic ring system containing 5-10 atoms, of which 0-3 are selected from nitrogen, oxygen and sulfur and the remainder are carbon (in particular, an aromatic ring system containing 6-10 atoms, of which 0-2 are nitrogen and the remainder are carbon), or Z completes a non-aromatic ring system containing 5-10 atoms, of which 0-3 are independently selected from oxygen, nitrogen and sulphur and the remainder are carbon. Examples of aromatic ring systems completed by Z include benzene, naphthalene, pyridine, quinoline, isoquinoline, pyrazine, pyrimidine, pyrrole, furan, thiophene, indole, benzofuran, benzothiophene, oxazole, isoxazole, thiazole, isothiazole and triazole. Examples of non-aromatic ring systems completed by Z include cyclohexane, cyclopentane, indane, tetralin, decalin, piperidine, piperazine, morpholine, tetrahydrofuran and tetrahydrothiophene. Preferably, Z completes a benzene ring or a pyridine ring.

$Z^1$ completes a non-aromatic ring system containing 5-10 atoms, of which 0-3 are independently selected from oxygen, nitrogen and sulphur and the remainder are carbon. Examples of ring systems completed by $Z^1$ include cyclohexane, cyclopentane, indane, tetralin, decalin, piperidine, piperazine, morpholine, tetrahydrofuran and tetrahydrothiophene.

$Z^2$ completes a heteroaromatic ring comprising 5 or 6 atoms, such as imidazole, triazole or pyrimidine.

A fused ring (as indicated by Z, $Z^1$ or $Z^2$) may form part of A or B, but A and B preferably do not both comprise such a ring. Typically, such fused rings (if present) form part of A.

Examples of structures completed by A and B include (but are not restricted to):

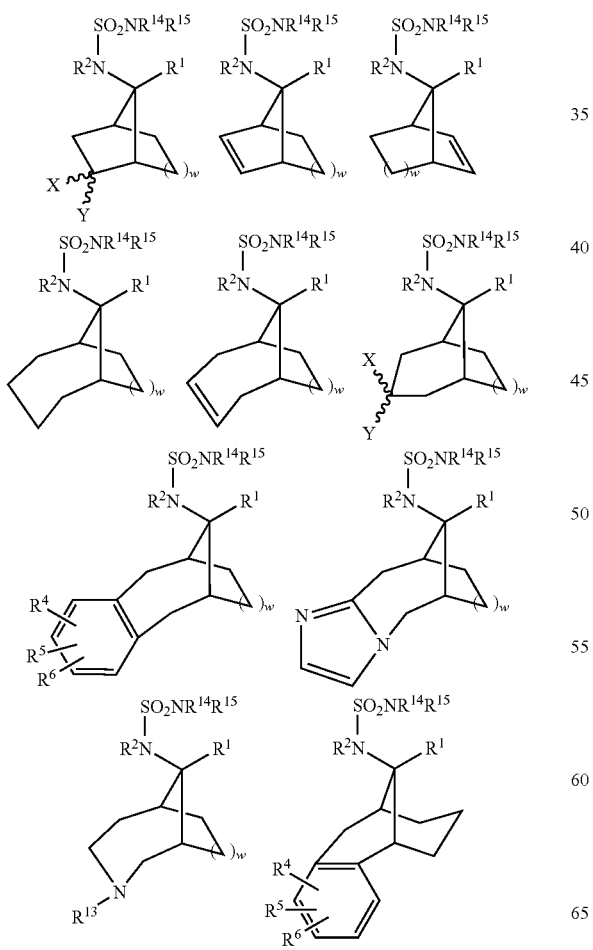

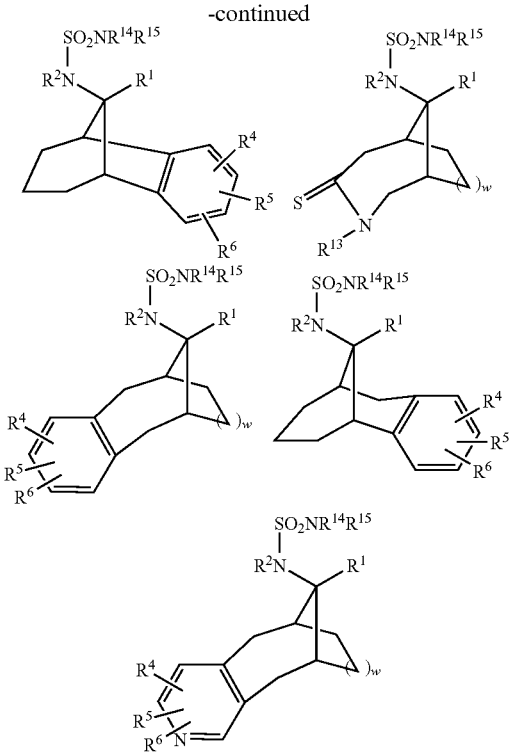

where w is 1 or 2, and X, Y, $R^1$, $R^2$, $R^4$, $R^5$, $R^6$, $R^{13}$, $R^{14}$ and $R^{15}$ have the same meanings as before.

Examples of preferred structures include:

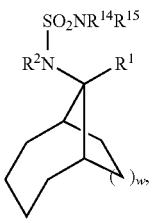

IA

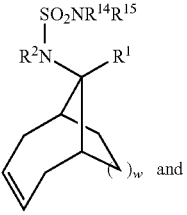

IB

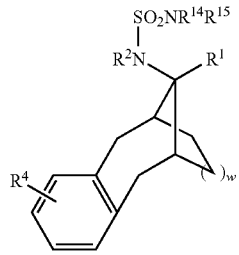

IC wherein w, $R^1$, $R^2$, $R^4$, $R^{14}$ and $R^{15}$ have the same meanings as before.

$R^1$ represents H, $C_{1-4}$alkyl (such as methyl, ethyl, isopropyl or t-butyl), $C_{2-4}$alkenyl (such as allyl), or $R^1$ and $R^{15}$ together complete a cyclic sulfamide containing 5, 6 or 7 ring atoms. Preferably, $R^1$ represents H, methyl or allyl, or together with $R^{15}$ completes a cyclic sulfamide containing 5 or 6 ring atoms. Most preferably, $R^1$ represents H, or together with $R^{15}$ completes a cyclic sulfamide containing 5 or 6 ring atoms.

$R^2$ represents H, $C_{1-6}$alkyl (such as methyl, ethyl, propyl or butyl), $C_{6-10}$aryl (such as phenyl or naphthyl), $C_{6-10}$aryl$C_{1-6}$alkyl (such as benzyl), $C_{3-6}$cycloalkyl (such as cyclopropyl, cyclopentyl or cyclohexyl), or $C_{2-6}$acyl which is optionally substituted with $CO_2H$ (such as acetyl, malonoyl, succinoyl or glutaroyl), or with an amino group, in particular a primary amino group or an alkyl- or dialkylamino group in which the alkyl group(s) comprise(s) up to 4 carbons. Preferably, $R^2$ is H.

$R^{14}$ represents H, $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, $C_{6-10}$aryl$C_{1-6}$alkyl, or heteroaryl$C_{1-6}$alkyl, wherein the alkyl, cycloalkyl, alkenyl and alkynyl groups optionally bear one substituent selected from halogen, CN, $NO_2$, $-OR^7$, $-SR^7$, $-S(O)_tR^8$ where t is 1 or 2, $-N(R^7)_2$, $-COR^7$, $-CO_2R^7$, $-OCOR^8$, $-CON(R^7)_2$, $-NR^7COR^8$, $-C_{1-6}$alkylNR$^7$COR$^8$, $-NR^7CO_2R^8$ and $-NR^7SO_2R^8$, and the aryl and heteroaryl groups optionally bear up to 3 substituents selected from $R^8$, halogen, CN, $NO_2$, $-OR^7$, $-SR^7$, $-S(O)_tR^8$ where t is 1 or 2, $-N(R^7)_2$, $-COR^7$, $-CO_2R^7$, $-OCOR^8$, $-CON(R^7)_2$, $-NR^7COR^8$, $-C_{1-6}$alkylNR$^7$COR$^8$, $-NR^7CO_2R^8$ and $-NR^7SO_2R^8$, where $R^7$ represents H or $R^8$; or two $R^7$ groups together with a nitrogen atom to which they are mutually attached may complete a pyrrolidine, piperidine, piperazine or morpholine ring, while $R^8$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, Ar or $-C_{1-6}$alkylAr, where Ar represents phenyl or heteroaryl either of which optionally bears up to 3 substituents independently selected from halogen, $CF_3$, $NO_2$, CN, $C_{1-6}$alkyl and $C_{1-6}$alkoxy. Preferably, $R^7$ and $R^8$ are independently selected from H, $C_{1-6}$alkyl (especially methyl, ethyl, n-propyl or isopropyl), perfluoro$C_{1-6}$alkyl (especially trifluoromethyl or 2,2,2-trifluoroethyl), Ar (especially phenyl optionally bearing up to 3 substituents independently selected from halogen, $CF_3$, $NO_2$, CN, $C_{1-6}$alkyl and $C_{1-6}$alkoxy) and $-C_{1-6}$alkylAr (especially benzyl optionally bearing up to 3 substituents independently selected from halogen, $CF_3$, $NO_2$, CN, $C_{1-6}$alkyl and $C_{1-6}$alkoxy), with the proviso that $R^8$ cannot be H.

$R^{14}$ preferably represents optionally substituted $C_{1-10}$alkyl (such as methyl, ethyl, n-propyl, isopropyl, n-butyl, t-butyl, sec-butyl, cyanomethyl, 2-fluoroethyl and methoxyethyl), perfluoro$C_{1-6}$alkyl (such as trifluoromethyl and 2,2,2-trifluoroethyl), $C_{3-10}$cycloalkyl (such as cyclopropyl, cyclobutyl, cyclopentyl and cyclohexyl), $C_{3-6}$cycloalkyl$C_{1-6}$alkyl (such as cyclopropylmethyl, cyclobutylmethyl and cyclopentylmethyl), $C_{2-6}$alkenyl (such as allyl), $C_{2-6}$alkynyl (such as propargyl), $C_{6-10}$aryl (such as phenyl) or $C_{6-10}$aryl$C_{1-6}$alkyl (such as benzyl which optionally bears up to 2 halogen substituents).

$R^{15}$ represents H or $C_{1-6}$alkyl (such as methyl or ethyl), preferably H. Alternatively, $R^{15}$ and $R^1$ together complete a cyclic sulfamide of 5, 6 or 7 ring atoms, preferably 5 or 6 ring atoms, and most preferably 5 ring atoms.

$R^4$, $R^5$ and $R^6$ independently represent $R^9$, halogen, CN, $NO_2$, $-OR^9$, $-SR^9$, $-S(O)_tR^{10}$ where t is 1 or 2, $-N(R^9)_2$, $-COR^9$, $-CO_2R^9$, $-OCOR^{10}$, $-CH=N-OR^{11}$, $-CON(R^9)_2$, $-SO_2N(R^9)_2$, $-NR^9COR^{10}$, $-NR^9CO_2R^{10}$, $-NR^9SO_2R^{10}$, $-CH=CHCH_2N(R^{16})_2$, $-CH_2OR^{10}$, $-CH_2N(R^{16})_2$, $-NHCOCH_2OR^{10}$ or $-NHCOCH_2N(R^{16})_2$; where $R^9$, $R^{10}$, $R^{11}$ and $R^{16}$ are as defined previously. When the group A or B comprises a non-aromatic ring completed by Z or $Z^1$, $R^4$, $R^5$ and $R^6$ preferably all represent hydrogen. When A or B comprises an aromatic ring completed by Z, $R^4$, $R^5$ and $R^6$ are preferably independently selected from $R^9$, halogen, CN, $NO_2$, $-OR^9$, $-N(R^9)_2$, $-NR^9COR^{10}$, $-NR^9CO_2R^{10}$, $-CH=N-OR^{10}$, $-CH=CHCH_2N(R^{16})_2$, $-CH_2OR^9$, $-CH_2N(R^{16})_2$, $-NHCOCH_2OR^{10}$ and $-NHCOCH_2N(R^{16})_2$, but preferably at least one of $R^5$ and $R^6$ represents H, and most preferably both of $R^5$ and $R^6$ represent H.

When A or B comprises a heteroaromatic ring completed by $Z^2$, $R^4$ preferably represents H.

$R^9$ represents H or $R^{10}$; or two $R^9$ groups together with a nitrogen atom to which they are mutually attached may complete a pyrrolidine, piperidine, piperazine or morpholine ring which is optionally substituted by $R^2$, $-COR^{12}$ or $-SO_2R^{12}$, while $R^{10}$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, heterocyclyl, $C_{6-10}$aryl$C_{1-6}$alkyl, heteroaryl$C_{1-6}$alkyl, heterocyclyl$C_{1-6}$alkyl, $C_{6-10}$aryl$C_{2-6}$alkenyl or heteroaryl$C_{2-6}$alkenyl, wherein the alkyl, cycloalkyl, alkenyl and alkynyl groups optionally bear one substituent selected from halogen, $CF_3$, $NO_2$, CN, $-OR^{11}$, $-SR^{11}$, $-SO_2R^{12}$, $-COR^{11}$, $-CO_2R^{11}$, $-CON(R^{11})_2$, $-OCOR^{12}$, $-N(R^{11})_2$ and $-NR^{11}COR^{12}$; and the aryl, heteroaryl and heterocyclic groups optionally bear up to 3 substituents independently selected from halogen, $NO_2$, CN, $R^2$, $-OR^{11}$, $-SR^{11}$, $-SO_2R^{12}$, $-COR^{11}$, $-CO_2R^{11}$, $-CON(R^{11})_2$, $-OCOR^{12}$, $-N(R^{11})_2$ and $-NR^{11}COR^{12}$, where $R^{11}$ and $R^{12}$ are as defined previously. Preferably, $R^9$ and $R^{10}$ independently represent H, $C_{1-10}$alkyl, perfluoro$C_{1-6}$alkyl, $C_{3-6}$cycloalkyl$C_{1-6}$alkyl, $C_{2-10}$alkenyl, $C_{2-10}$alkynyl, $C_{6-10}$aryl, heteroaryl, heterocyclyl, $C_{6-10}$aryl$C_{1-6}$alkyl, $C_{6-10}$aryl$C_{2-6}$alkenyl, heteroaryl$C_{2-6}$alkenyl, heterocyclyl$C_{1-6}$alkyl or heteroaryl$C_{1-6}$alkyl, wherein the alkyl, cycloalkyl, alkenyl and alkynyl groups are unsubstituted or substituted by CN, $-OR^{11}$, $-N(R^{11})_2$, $-COR^{11}$, $-CO_2R^{11}$ or $-CON(R^{11})_2$, and wherein the aryl, heteroaryl and heterocyclyl groups bear not more than two substituents selected from halogen, $NO_2$, CN, $R^{12}$, $-OR^{11}$ and $-SO_2R^2$, with the proviso that $R^{10}$ cannot represent H.

$R^{11}$ represents H or $R^{12}$; or two $R^{11}$ groups together with a nitrogen atom to which they are mutually attached may complete a heterocyclic ring system of 3-10 atoms, 0-2 of which (in addition to said nitrogen atom) are selected from O, N and S, said ring system bearing 0-2 substituents selected from halogen, CN, $NO_2$, oxo, $R^{12}$, OH, $OR^{12}$, $NH_2$, $NHR^{12}$, CHO, $CO_2H$, $COR^{12}$ and $CO_2R^{12}$; while $R^{12}$ represents $C_{1-6}$alkyl which is optionally substituted with halogen, CN, OH, $C_{1-4}$alkoxy or $C_{1-4}$alkoxycarbonyl; $C_{3-7}$cycloalkyl, perfluoro$C_{1-6}$alkyl, $C_{2-6}$alkenyl, $C_{2-6}$alkynyl, ArO$C_{1-6}$alkyl, Ar, $-C_{1-6}$alkylAr, or C-heterocyclyl which is optionally substituted with halogen, CN, $C_{1-6}$alkyl, OH, perfluoro$C_{1-6}$alkyl, $C_{2-6}$acyl, $C_{1-4}$alkoxy or $C_{1-4}$alkoxycarbonyl; where Ar represents phenyl or heteroaryl either of which optionally bears up to 3 substituents independently selected from halogen, $CF_3$, $NO_2$, CN, $OCF_3$, $C_{1-6}$alkyl and $C_{1-6}$alkoxy. Preferably, $R^{11}$ and $R^{12}$ independently represent H, optionally substituted $C_{1-6}$alkyl, perfluoro$C_{1-6}$alkyl, $C_{2-6}$alkenyl, $C_{2-6}$alkynyl, phenyl (optionally bearing up to 2 substituents independently selected from halogen, $CF_3$, $NO_2$, CN, $C_{1-6}$alkyl and $C_{1-6}$alkoxy), heteroaryl (optionally substituted by halogen, $CF_3$ or $C_{1-6}$alkyl), heteroaryl$C_{1-6}$alkyl (such as pyridylmethyl or thienylmethyl), benzyl (optionally bearing up to 2 substituents independently selected from halogen, $CF_3$, $NO_2$, CN, $C_{1-6}$alkyl and $C_{1-6}$alkoxy), or optionally-substituted C-heterocyclyl (such as piperidin-4-yl or 1-acetylpiperidin-4-yl), with the proviso that $R^{12}$ cannot represent H. Alternatively, two $R^{11}$ groups together with a nitrogen atom to which they are mutually attached complete a heterocyclic ring system. Examples of heterocyclic groups represented by $N(R^{11})_2$ include morpholin-4-yl, pyrrolidin-1-yl, 2-oxopyrrolidin-1-yl, 2-oxo-imidazolin-1-yl, piperidin-1-yl, 4,4-difluoropiperidin-1-yl, 4-trifluoromethylpiperidin-1-yl, 5-aza-2-oxa-[2.2.1]bicyclohept-5-yl, piperazin-1-yl, 4-methylpiperazin-1-yl, 3-oxo-4-phenylpiperazin-1-yl and 4-acetylpiperazin-1-yl.

Each $R^{16}$ independently represents H or $R^{10}$, or two $R^{16}$ groups together with the nitrogen to which they are mutually attached complete a mono- or bicyclic heterocyclic ring system of 5-10 ring atoms selected from C, N, O and S, said ring system optionally having an additional aryl or heteroaryl ring fused thereto, said heterocyclic system and optional fused ring bearing 0-3 substituents independently selected from halogen, oxo, $NO_2$, CN, $R^2$, $—OR^{11}$, $—SR^{11}$, $—SO_2R^{12}$, $—COR^{11}$, $—CO_2R^{11}$, $—CON(R^{11})_2$, $—OCOR^{12}$, $—N(R^{11})_2$ and $—NR^{11}COR^{12}$. Examples of heterocyclic ring systems represented by $—N(R^{16})_2$ include pyrrolidine, piperidine, piperazine, morpholine, thiomorpholine, 2,5-diazabicyclo[2,2,1]heptane, 5,6-dihydro-8H-imidazo[1,2-a]pyrazine and spiro[isobenzofuran-1(3H), 4'-piperidine]. Preferred substituents include halogen, OH, oxo and $R^{12}$ groups, such as alkyl, cycloalkyl, perfluoroalkyl, phenoxyalkyl, pyridyl and phenyl, wherein the pyridyl and phenyl groups optionally bear up to 2 substituents selected from halogen (especially chlorine or fluorine), $C_{1-6}$alkyl and $C_{1-6}$alkoxy.

$R^4$ very aptly represents halogen (especially chlorine, bromine or fluorine), nitro, CN, phenyl, substituted phenyl (such as 3,5-bis(trifluoromethyl)phenyl, o-anisyl, 2-fluorophenyl, 3-fluorophenyl and 4-fluorophenyl), heteroaryl, oximino or alkoximino represented by $—CH=NOR^{11}$, amino represented by $—N(R^9)_2$, amido represented by $—NR^9COR^{10}$, carbamate represented by $—NR^9CO_2R^{10}$, alkoxy represented by $—OR^{10}$, optionally substituted alkenyl, including $—CH=CHCH_2N(R^{16})_2C_{6-10}arylC_{2-6}alkenyl$ and heteroaryl$C_{2-6}$alkenyl, substituted acetamido represented by $—NHCOCH_2(NR^{16})_2$ and $—NHCOCH_2OR^{10}$, or substituted methyl represented by $—CH_2OR^9$.

$R^4$ also very aptly represents H, OH, CHO, $CO_2H$, alkoxycarbonyl represented by $CO_2R^{10}$ (such as methoxycarbonyl and ethoxycarbonyl) or substituted $C_{1-6}$alkyl (in particular, $C_{1-6}$alkyl which is substituted by $—CO_2R^{11}$ or $—N(R^{11})_2$).

Heteroaryl groups represented by $R^4$ are typically 5- or 6-membered rings such as optionally-substituted (and optionally benzo-fused) pyridine, furan, thiophene, pyrrole, pyrazole, imidazole, triazole, oxazole, isoxazole, thiazole, isothiazole, oxadiazole and thiadiazole. A particular subclass of heteroaryl groups represented by $R^4$ are 5-membered heteroaryl rings which are optionally substituted with Ar. Ar in this context typically represents (but is not restricted to) phenyl, halophenyl, pyridyl or pyrazinyl. Examples of heteroaryl groups within this class include 5-phenyl-1,2,4-oxadiazol-3-yl, 5-(4-fluorophenyl)-1,2,4-oxadiazol-3-yl, 5-phenyl-1,3,4-oxadiazol-2-yl, 5-(4-fluorophenyl)-1,3,4-oxadiazol-2-yl, 5-pyridyl-1,2,4-oxadiazol-3-yl, 3-(4-fluorophenyl)-1,2,4-oxadiazol-5-yl, 5-(4-fluorophenyl)oxazol-2-yl, 3-(pyridin-2-yl)-1,2,4-oxadiazol-5-yl, 3-pyrazinyl-1,2,4-oxadiazol-5-yl, and 5-(4-fluorophenyl)pyrazol-3-yl. Examples of other heteroaryl groups represented by $R^4$ include 3-thienyl, 2-thienyl, 2-benzofuryl, 4-pyridyl, 3-pyridyl and 6-methoxy-3-pyridyl.

Examples of oximino or alkoximino groups represented by $R^4$ include $CH=NOH$, $—CH=NOC_2H_5$, $—CH=NOCH_2CH=CH_2$ and $—CH=NOCH_2Ar$. In this context, Ar typically represents (but is not restricted to) a phenyl group bearing 0-2 substituents selected from halogen and $CF_3$.

Typical examples of amino groups represented by $R^4$ include $NH_2$, (3-pyridylmethyl)amino, 4-phenoxybenzylamino, 4-benzyloxybenzylamino, 2-methoxybenzylamino, 3-methoxybenzylamino, 4-methoxybenzylamino, 3,3-dimethylbutylamino, (cyclohexylmethyl)amino, 3-methylbutylamino, (4-pyridylmethyl)amino, 2-benzyloxyethylamino, 2-phenylpropylamino, (2,3-dihydrobenzo[1,4]dioxin-6-ylmethyl)amino, 4-t-butylbenzylamino, 3-phenylbutylamino, 4-isopropoxybenzylamino, (benzofuran-2-ylmethyl)amino, 3-phenylpropylamino, 4-n-pentylbenzylamino, 4-methanesulphonylbenzylamino, 3-(4-t-butylphenoxy)benzylamino, 3-(4-methoxyphenoxy)benzylamino, 3-trifluoromethoxybenzylamino, 4-cyanobenzylamino, 3-fluorobenzylamino, 4-fluorobenzylamino, 3-chlorobenzylamino, 3-trifluoromethylbenzylamino, 3-(3,4-dichlorophenoxy)benzylamino, 4-(4-t-butylthiazol-2-yl)benzylamino, 4-(hex-1-ynyl)benzylamino, 3-benzyloxybenzylamino and 4-phenylpiperidin-1-yl.

Typical examples of amide groups represented by $R^4$ include benzamido, phenylacetamido, 3,5-difluorophenylacetamido, 4-fluorobenzamido, acetamido, propionamido, butyramido, pentanamido, hexanamido, isobutyramido, 3-methylbutyramido, 2-methylbutyramido, 2-methylpentanamido, 3-methylpentanamido, 4-methylpentanamido, 2,2-dimethylbutyramido, 2-ethylbutyramido, cyclopentylacetamido, 2,2-dimethylpent-4-enamido, cyclopropylacetamido, 4-methyloctanamido, 3,5,5-trimethylhexanamido, 2-methylhexanamido, 2,2-dimethylpentanamido, 5-methylhexanamido, 3-phenylpropionamido, isonicotinamido, pyridine-2-carboxamido, nicotinamido and 2-(2,4-dichlorophenoxy)propionamido.

Typical examples of carbamate groups represented by $R^4$ include phenoxycarbonylamino, 4-chlorophenoxycarbonylamino, methoxycarbonylamino, benzyloxycarbonylamino, isobutoxycarbonylamino, allyloxycarbonylamino, 4-methylphenoxycarbonylamino, 4-bromophenoxycarbonylamino, 4-fluorophenoxycarbonylamino, 4-methoxyphenoxycarbonylamino and 2,2-dimethylpropoxycarbonylamino.

When $R^4$ represents an alkoxy group $—OR^{10}$, $R^{10}$ preferably represents $C_{6-10}arylC_{1-6}alkyl$ (such as benzyl, chlorobenzyl, fluorobenzyl and methoxybenzyl), heteroaryl$C_{1-6}$alkyl (such as pyridylmethyl and pyridylethyl), $C_{1-6}$alkyl (such as methyl), or $C_{1-6}$alkyl which is substituted with $—OR^{11}$ or with $—N(R^{11})_2$, especially an ethyl group substituted in the 2-position with $—OAr$ or with $—N(R^{11})_2$ where the $R^{11}$ groups optionally complete a heterocyclic ring. Examples of substituted ethoxy groups represented by $R^4$ include phenoxyethoxy, 4-chlorophenoxyethoxy, 4-fluorophenoxyethoxy, imidazol-1-ylethoxy, pyridin-2-ylethoxy and $—OCH_2CH_2—N(R^{11})_2$ in which $—N(R^{11})_2$ represents morpholin-4-yl, 4-acetylpiperazin-1-yl, 4-trifluoromethylpiperidin-1-yl, N-(thiophene-2-ylmethyl)amino, N-(pyridin-3-ylmethyl)amino, 2-oxopyrrolidin-1-yl, 2-oxoimidazolin-1-yl or 3-oxo-4-phenylpiperazin-1-yl.

Typical examples of $C_{6-10}arylC_{2-6}$alkenyl groups represented by $R^4$ include 4-phenylbut-1-enyl, styryl, 4-methoxystyryl, 4-fluorostyryl, 4-chlorostyryl and 4-bromostyryl.

Typical examples of heteroaryl$C_{2-6}$alkenyl groups represented by $R^4$ include 3-(imidazol-1-yl)propenyl and 3-(1,2,4-triazol-1-yl)propenyl.

Typical examples of alkenyl and substituted alkenyl groups represented by $R^4$ include, vinyl, cyanovinyl, 3-hydroxypropenyl, methoxycarbonylethenyl, benzoylethenyl and 3-[4-methyl-1,2,4-triazol-5-ylthio]propenyl.

A special class of alkenyl groups represented by $R^4$ have the formula —CH=CHCH$_2$N($R^{16}$)$_2$. In this context, typical embodiments of —N($R^{16}$)$_2$ include N,N-dimethylamino, piperidin-1-yl, morpholin-4-yl, 4-methylpiperazin-1-yl, 4-phenylpiperazin-1-yl and N-(2-methoxyethyl)-N-methylamino. Further examples include 4-trifluoromethylpiperidin-1-yl, 4,4-difluoropiperidin-1-yl, 5-aza-2-oxabicyclo[2.2.1]hept-5-yl, 1,2,3,6-tetrahydropyridin-1-yl, N-furfurylamino, N-(indan-1-yl)amino, N-(pyridin-2-ylmethyl)amino, N,N-bis(2-methoxyethyl)amino, 3,3-difluoropyrrolidin-1-yl, 4-hydroxy-4-trifluoromethylpiperidin-1-yl, 3-oxopiperazin-1-yl, 3-oxo-4-cyclohexylpiperazin-1-yl, 3-oxo-4-phenylpiperazin-1-yl, 4-methylpiperidin-1-yl, N-(2,2,2-trifluoroethyl)amino, N-(thiophene-2-ylmethyl)amino, N-methyl-N-(tetrahydrofuran-3-ylmethyl)amino, 2-phenoxymethylmorpholin-4-yl, 3-(pyridin-3-yl)-pyrrolidin-1-yl, N-(4-phenylmorpholin-2-ylmethyl)amino, N-(tetrahydropyran-2-ylmethyl)amino, N-(tetrahydrofuran-3-yl)amino, 3-hydroxypiperidin-1-yl, N-methyl-N-(tetrahydropyran-4-yl)amino, N-(dioxan-2-ylmethyl)amino and N-(tetrahydropyran-4-yl)amino.

Typical examples of substituted acetamido groups represented by —NHCOCH$_2$(N$R^{16}$)$_2$ include 2-(diethylamino)acetamido, 2-(N-benzyl-N-methylamino)acetamido, 2-(pyrrolidin-1-yl)acetamido, 2-[4-(4-fluorophenyl)piperazin-1-yl]acetamido, 2-[5-(4-fluorophenyl)-2,5-diazabicyclo[2.2.1]hept-2-yl]acetamido, 2-(4-phenylpiperazin-1-yl)acetamido, 2-(piperidin-1-yl)acetamido, 2-(4-methylpiperazin-1-yl)acetamido, 2-(morpholin-4-yl)acetamido, 2-(4-phenylpiperidin-1-yl)acetamido, 2-[4-(2-methoxyphenyl)piperidin-1-yl]acetamido, 2-(2-phenoxymethylmorpholin-4-yl)acetamido, 2-[(4-phenylmorpholin-2-ylmethyl)amino]acetamido, 2-(3-phenyl-5,6-dihydro-8H-imidazo[1,2-a]pyrazin-7-yl)acetamido and 2-[4-(2-methoxyphenyl)piperazin-1-yl]acetamido.

Typical examples of substituted acetamido groups represented by —NHCOCH$_2$O$R^{10}$ include 2-methoxyacetamido, 2-phenoxyacetamido, and the corresponding 2-, 3- and 4-fluorophenoxy derivatives and 2-, 3- and 4-chlorophenoxy derivatives.

Typical examples of substituted methyl groups represented by —CH$_2$O$R^9$ include hydroxymethyl, phenoxymethyl, 2-, 3- and 4-chlorophenoxymethyl, 2-, 3- and 4-fluorophenoxymethyl, 2-, 3- and 4-methoxyphenoxymethyl, 4-trifluoromethylphenoxymethyl, 4-t-butylphenoxymethyl, 4-[1,2,4]triazol-1-ylphenoxymethyl, quinolin-5-yloxymethyl, 4-trifluoromethoxyphenoxymethyl and 4-(4-acetylpiperazin-1-yl)phenoxymethyl.

Typical examples of other substituted $C_{1-6}$alkyl groups represented by $R^4$ include 3-(morpholin-4-yl)propyl, 3-(4-trifluoromethylpiperidin-1-yl)propyl, morpholin-4-ylmethyl, 2-carboxyethyl and 2-methoxycarbonylethyl.

A preferred subset of the compounds of formula I are those defined by embodiment (A):

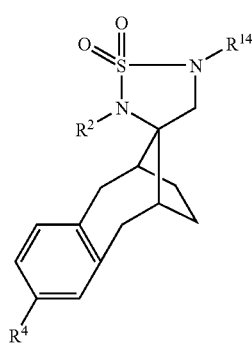

(A)

wherein $R^2$, $R^4$ and $R^{14}$ have the same meanings and preferred identities as before. Preferably, $R^2$ represents H or $C_{2-6}$acyl which is optionally substituted with a carboxylic acid group or with an amino group; and most preferably $R^2$ represents H. In one sub-embodiment, $R^4$ represents a 5-membered heteroaryl ring which is optionally substituted with Ar where Ar has the same meaning and preferred identities as before.

In particular examples of embodiment (A), $R^4$, $R^2$ and $R^{14}$ are as follows:

| $R^{14}$ | $R^2$ | $R^4$ |
|---|---|---|
| ethyl | H | H |
| n-propyl | H | H |
| n-butyl | H | H |
| 2,2,2-trifluoroethyl | H | H |
| n-propyl | H | PhCH$_2$O— |
| n-propyl | H | F—C$_6$H$_4$—O—CH$_2$CH$_2$—O—CH$_3$ |
| n-propyl | acetyl | H |

In further examples of embodiment (A), $R^2$ and $R^4$ are both H and $R^{14}$ is isopropyl, 2-methylpropyl, 2-fluoroethyl, cyclopropylmethyl, cyclobutylmethyl, cyclopentylmethyl, cyclohexylmethyl, cyclobutyl or cyclopentyl.

In further examples of embodiment (A), $R^2$ is H, $R^4$ is PhCH$_2$O—, and $R^{14}$ is cyclobutylmethyl, 2,2,2-trifluoroethyl, phenyl, benzyl, 3,4-difluorobenzyl, 2,5-difluorobenzyl or 4-chlorobenzyl.

In further examples of embodiment (A), $R^2$ is H, $R^{14}$ is n-propyl, and $R^4$ is 3-pyridyl, (pyridin-3-yl)methoxy, —CO$_2$Me, 2-(pyridin-2-yl)ethoxy, 3-(morpholin-4-yl)propyl, —CH$_2$OH, —CHO, —CH=CHCO$_2$Me, 3-[(4-methyl-1,2,4-triazol-3-yl)thio]prop-1-enyl, —CN, 5-(4-fluorophenyl)oxazol-2-yl, 5-(4-fluorophenyl)-1,3,4-oxadiazol-2-yl, 3-(pyridin-2-yl)-1,2,4-oxadiazol-5-yl, 3-pyrazinyl-1,2,4-oxadiazol-5-yl, —CH=CHCH$_2$OH, or 5-(4-fluorophenyl)pyrazol-3-yl.

In further examples of embodiment (A), $R^2$ is H, $R^{14}$ is n-propyl, and $R^4$ is —CH=CHCH$_2$N($R^{16}$)$_2$ where —N($R^{16}$)$_2$ is morpholin-4-yl, 4-trifluoromethylpiperidin-1-yl, 4,4-difluoropiperidin-1-yl, 4-carbamoylpiperidin-1-yl, 4-ethoxycarbonylpiperidin-1-yl, 4-carboxypiperidin-1-yl, 4-hydroxypiperidin-1-yl, 1,2,3,6-tetrahydropyridinyl, 5-aza-2-oxabicyclo[2.2.1]hept-1-yl, N-[(furan-2-yl)methyl]amino, N,N-bis(2-methoxyethyl)amino, N-(indan-1-yl)amino, or N-[(pyridin-2-yl)methyl]amino.

In further examples of embodiment (A), $R^2$ is H, $R^{14}$ is n-propyl, and $R^4$ is —OCH$_2$CH$_2$N($R^{11}$)$_2$ where —N($R^{11}$)$_2$ is morpholin-4-yl, or 2-oxo-imidazolin-1-yl.

In further examples of embodiment (A), $R^2$ is H, $R^{14}$ is 2,2,2-trifluoroethyl and $R^4$ is —OH, —CO$_2$Me, —CH$_2$OH, —CHO, —CO$_2$H, —CH=CHCO$_2$Me, —CH=CHCO$_2$H, —CH=CHCH$_2$OH, —CH=N—OH, —CH=N—OEt, —CH$_2$CH$_2$CO$_2$Me, —CH$_2$CH$_2$CO$_2$H, (morpholin-4-yl)methyl, 2-(imidazol-1-yl)ethoxy, 3-(4-trifluoromethylpiperidin-1-yl)propyl, —CH=N—OCH$_2$Ph, —CH=N—OCH$_2$(4-F—C$_6$H$_4$), —CH=N—OCH$_2$(4-CF$_3$—C$_6$H$_4$), 3-pyrazinyl-1,2,4-oxadiazol-5-yl, 3-(4-fluorophenyl)-1,2,4-oxadiazol-5-yl, 3-(pyridin-2-yl)-1,2,4-oxadiazol-5-yl, —CH=N—OCH$_2$(2-F—C$_6$H$_4$), —CH=N—OCH$_2$CH=CH$_2$, —CH=N—OCH$_2$(3-F—C$_6$H$_4$), or —CH=N—OCH$_2$(2,4-di-C$_1$-C$_6$H$_3$).

In further examples of embodiment (A), $R^2$ is H, $R^{14}$ is 2,2,2-trifluoroethyl and $R^4$ is —CH=CHCH$_2$N($R^{16}$)$_2$ where —N($R^{16}$)$_2$ is morpholin-4-yl, 4-trifluoromethylpiperidin-1-yl, 5-aza-2-oxabicyclo[2.2.1]hept-1-yl, 4,4-difluoropiperidin-1-yl, 4-hydroxy-4-trifluoromethylpiperidin-1-yl, 4-methylpiperidin-1-yl, 3-oxo-4-phenylpiperazin-1-yl, 3-oxo-4-cyclohexylpiperazin-1-yl, 3-oxo-piperazin-1-yl, N-(tetrahydrofuran-3-yl)amino, N-methyl-N-(tetrahydrofuran-3-yl)amino, N-(tetrahydropyran-4-yl)amino, N-methyl-N-(tetrahydropyran-4-yl)amino, N-(dioxanylmethyl)amino, N-[(tetrahydropyran-2-yl)methyl]amino, 3-hydroxypiperidin-1-yl, 5-aza-2-oxabicyclo[5.4.0]undeca-7,9,11-trien-5-yl, 2-(phenoxymethyl)morpholin-4-yl, N-[(4-phenylmorpholin-2-yl)methyl]amino, 3,3-difluoropyrrolidin-1-yl, N-(2,2,2-trifluoroethyl)amino, or 3-(pyridin-3-yl)pyrrolidin-1-yl.

In further examples of embodiment (A), $R^2$ is H, $R^{14}$ is 2,2,2-trifluoroethyl and $R^4$ is —OCH$_2$CH$_2$N($R^{11}$)$_2$ where N($R^{11}$)$_2$ is morpholin-1-yl, 4-acetylpiperazin-1-yl, N-(2-methoxyethyl)amino, N-[(thiophen-2-yl)methyl]amino, N-[(pyridin-3-yl)methyl]amino, N-(methoxycarbonylmethyl)amino, 3-oxo-4-phenylpiperazin-1-yl, or 4-trifluoromethypiperidin-1-yl.

The synthesis of these and other compounds in accordance with formula I is described in WO 02/36555, the contents of which are incorporated herein by reference.

Another preferred subset of the compounds of formula I are those defined by formula II:

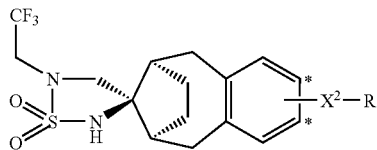

II wherein the moiety $X^2$—R is attached at one of the positions indicated by an asterisk;
$X^2$ is a bivalent pyrazole, imidazole, triazole, oxazole, isoxazole, thiazole, isothiazole, thiadiazole or 1,3,4-oxadiazole residue optionally bearing a hydrocarbon substituent comprising 1-5 carbon atoms which is optionally substituted with up to 3 halogen atoms; and
R is selected from:
  (i) CF$_3$ or an alkyl group of up to 6 carbon atoms, optionally substituted with halogen, CF$_3$, CHF$_2$, CN, OH, CO$_2$H, C$_{2-6}$acyl, C$_{1-4}$alkoxy or C$_{1-4}$alkoxycarbonyl;
  (ii) a non-aromatic heterocyclic group comprising up to 7 ring atoms of which up to 3 are chosen from N, O and S and the remainder are carbon, bearing 0-3 substituents independently selected from oxo, halogen, CN, C$_{1-6}$alkyl, OH, CF$_3$, CHF$_2$, CH$_2$F, C$_{2-6}$acyl, CO$_2$H, C$_{1-4}$alkoxy and C$_{1-4}$alkoxycarbonyl;
  (iii) phenyl or 6-membered heteroaryl, either of which bears 0-3 substituents independently selected from halogen, CF$_3$, CHF$_2$, CH$_2$F, NO$_2$, CN, OCF$_3$, C$_{1-6}$alkyl and C$_{1-6}$alkoxy; and
  (iv) N($R^a$)$_2$ where each $R^a$ independently represents H or C$_{1-6}$alkyl which is optionally substituted with halogen, CF$_3$, CHF$_2$, CN, OH, C$_{1-4}$alkoxy or C$_{1-4}$alkoxycarbonyl;
or a pharmaceutically acceptable salt thereof.

It will be readily apparent to those skilled in the art that the compounds of formula II exist in two enantiomeric forms, depending on which of the ring positions indicated by an asterisk is bonded to the moiety —$X^2$—R. Attachment at the position indicated by the upper asterisk in formula I gives rise to a 2-substituted-[6S,9R,11R]2',3',4',5,5',6,7,8,9,10-decahydro-5'-(2,2,2-trifluoroethyl)-spiro[6,9-methanobenzocyclooctene-11,3'-[1,2,5]thiadiazole]1',1'-dioxide. Conversely, attachment at the position indicated by the lower asterisk in formula I gives rise to a 2-substituted-[6R,9S,11S]2',3',4',5,5',6,7,8,9,10-decahydro-5'-(2,2,2-trifluoroethyl)-spiro[6,9-methanobenzocyclooctene-11,3'-[1,2,5]thiadiazole]1',1'-dioxide. It is to be emphasised that the invention, for each identity of —$X^2$—R, encompasses both enantiomers, either as homochiral compounds or as mixtures of enantiomers in any proportion. Furthermore, structural formulae depicting attachment of —$X^2$—R or a synthetic precursor thereof at one of the said ring positions shall hereinafter be indicative of attachment at either of said ring positions, unless expressly stated otherwise.

In the compounds of formula II, $X^2$ is a bivalent pyrazole, imidazole, triazole, oxazole, isoxazole, thiazole, isothiazole, thiadiazole or 1,3,4-oxadiazole residue, optionally bearing a hydrocarbon substituent as defined previously. $X^2$ may be bonded to R and to the fused benzene ring via any of the available ring positions of $X^2$. Typically, $X^2$ is bonded both to R and to the fused benzene ring via carbon atoms, but when $X^2$ is a pyrazole, imidazole or triazole residue, one of the points of attachment may be a nitrogen atom. Preferably, the points of attachment do not occupy adjacent ring atoms of $X^2$.

The ring represented by $X^2$ optionally bears a hydrocarbon substituent comprising 1 to 5 carbon atoms, optionally substituted with up to 3 halogen atoms. Said optional hydrocarbon substituent may be attached to one of the ring carbon atoms of $X^2$, or when $X^2$ is a pyrazole, imidazole or triazole residue and both of its points of attachment are carbon atoms, it may be attached to one of the ring nitrogen atoms of $X^2$. In either case, the optional hydrocarbon substituent may comprise cyclic or acyclic hydrocarbon residues or combinations thereof, saturated or unsaturated, up to a maximum of 5 carbon atoms in total. The optional hydrocarbon substituent is preferably unsubstituted or is substituted with up to 3 fluorine atoms Examples include methyl, ethyl, n-propyl, isopropyl, n-butyl, sec-butyl, t-butyl, fluoromethyl, difluoromethyl, trifluoromethyl, 2,2,2-trifluoroethyl, cyclopropyl, cyclopropylmethyl and allyl. A preferred example is methyl.

When $X^2$ is a triazole or thiadiazole residue, both of the possible isomeric forms are within the scope of the invention. Thus, the definition of $X^2$ encompasses both 1,2,3- and 1,2,4-triazole residues, and both 1,2,4- and 1,3,4-thiadiazole residues.

Suitable identities for $X^2$ include 1,3,4-oxadiazol-2-yl, 1,3,4-thiadiazol-2-yl, 1,3,4-triazol-2-yl, 1,2,3-triazol-4-yl, 1,2,3-triazol-1-yl, 1,2,4-triazol-3-yl, 1-methyl-1,2,4-triazol-3-yl, oxazol-2-yl, pyrazol-3-yl, 1-methylpyrazol-3-yl, 1-methylpyrazol-5-yl, 1-ethylpyrazol-3-yl, 1-(2,2,2-trifluoroethyl)pyrazol-3-yl, thiazol-2-yl, 4-methylthiazol-2-yl, isoxazol-5-yl, isoxazol-3-yl, imidazol-2-yl, imidazol-4-yl and imidazol-1-yl, wherein the numbering indicates the ring atom of $X^2$ which is attached to the fused benzene ring in formula II.

Preferred identities for $X^2$ include 1-methyl-1,2,4-triazol-3-yl, 1-methylpyrazol-3-yl, 1-ethylpyrazol-3-yl, oxazol-2-yl, thiazol-2-yl and 4-methylthiazol-2-yl, in which R is attached to the 5-position of $X^2$. A further preferred identity for $X^2$ is imidazol-4-yl in which R is attached to the 1-position of $X^2$. Another preferred identity for $X^2$ is 1,2,4-triazol-3-yl in which R is attached to the 1-position of $X^2$.

A particularly preferred identity for $X^2$ is 1-methylpyrazol-3-yl in which R is attached to the 5-position.

In one embodiment, R is CF$_3$ or an alkyl group of up to 6 carbon atoms, optionally substituted with halogen, CF$_3$, CHF$_2$, CN, OH, CO$_2$H, C$_{2-6}$acyl, C$_{1-4}$alkoxy or C$_{1-4}$alkoxycarbonyl. Suitable examples include alkyl groups such as methyl, ethyl, n-propyl, isopropyl, n-butyl, sec-butyl, t-butyl and 2-methylpropyl. Within this embodiment, R very aptly represents CF$_3$ or t-butyl or isopropyl.

In a second embodiment, R represents a non-aromatic heterocyclic group comprising up to 7 ring atoms of which up to 3 are chosen from N, O and S and the remainder are carbon, bearing 0-3 substituents independently selected from oxo, halogen, CN, C$_{1-6}$alkyl, OH, CF$_3$, CHF$_2$, CH$_2$F, C$_{2-6}$acyl, CO$_2$H, C$_{1-4}$alkoxy and C$_{1-4}$alkoxycarbonyl. Suitable heterocyclic groups include azetidine, pyrrolidine, piperidine, tetrahydropyridine, piperazine, morpholine, thiomorpholine, thiomorpholine-1,1-dioxide, pyran and thiopyran. Heterocyclic groups containing one or more nitrogen atoms may be bonded to X$^2$ via carbon or via nitrogen. Within this embodiment, R very aptly represents piperidin-1-yl, 4-trifluoromethylpiperidin-1-yl, 4,4-difluoropiperidin-1-yl, 3,3-difluoropiperidin-1-yl, 3,3-difluoroazetidin-1-yl, morpholin-4-yl, 1-acetylpiperidin-4-yl, 1-trifluoroacetylpiperidin-4-yl, 1,2,3,6-tetrahydropyridin-4-yl, 1-trifluoroacetyl-1,2,3,6-tetrahydropyridin-4-yl or 1-(t-butoxycarbonyl)-1,2,3,6-tetrahydropyridin-4-yl. In a particular embodiment, when R represents an N-heterocyclyl group, X$^2$ is an oxazole or thiazole residue, preferably thiazol-2-yl in which R is attached to the 5-position.

In a third embodiment, R represents phenyl or 6-membered heteroaryl, either of which bears 0-3 substituents independently selected from halogen, CF$_3$, CHF$_2$, CH$_2$F, NO$_2$, CN, OCF$_3$, C$_{1-6}$alkyl and C$_{1-6}$alkoxy. Examples of suitable 6-membered heteroaryl groups represented by R include pyridyl, pyrazinyl, pyrimidinyl, pyridazinyl and triazinyl. Preferably, the phenyl or heteroaryl ring bears 0 to 2 substituents. Phenyl groups represented by R preferably bear at least one substituent. Preferred substituents include halogen (especially chlorine and fluorine), CN, C$_{1-6}$alkyl (especially methyl), C$_{1-6}$alkoxy (especially methoxy), OCF$_3$ and CF$_3$. If two or more substituents are present, preferably not more than one of them is other than halogen or alkyl. Within this embodiment, examples of groups represented by R include phenyl, monohalophenyl, dihalophenyl, trihalophenyl, cyanophenyl, methylphenyl, methoxyphenyl, trifluoromethylphenyl, trifluoromethoxyphenyl, pyridyl, monohalopyridyl and trifluoromethylpyridyl, wherein "halo" refers to fluoro or chloro. Suitable specific values for R include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 3,4,5-trifluorophenyl, 4-cyanophenyl, 4-methylphenyl, 4-methoxyphenyl, 2-(trifluoromethyl)phenyl, 4-(trifluoromethyl)phenyl, 4-(trifluoromethoxy)phenyl, pyridin-2-yl, pyridin-3-yl, pyridin-4-yl, pyrazin-2-yl, 5-methylpyridin-2-yl, 5-fluoropyridin-2-yl, 5-chloropyridin-2-yl, 5-(trifluoromethyl)pyridin-2-yl and 6-(trifluoromethyl)pyridin-3-yl. Preferred examples include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 4-(trifluoromethyl)phenyl, pyridin-2-yl, pyridin-3-yl and pyridin-4-yl.

In a fourth embodiment, R represents N(R$^a$)$_2$ where each R$^a$ independently represents H or C$_{1-6}$alkyl which is optionally substituted as defined previously. R$^a$ aptly represents H, unsubstituted alkyl such as methyl, ethyl, propyl or butyl, or haloalkyl such as mono-, di- or trifluoroethyl. Within this embodiment, R very aptly represents dimethylamino. In a particular embodiment, when R represents N(R$^a$)$_2$, X$^2$ is an oxazole or thiazole residue, preferably thiazol-2-yl wherein R is attached to the 5-position.

In one preferred embodiment of Formula II, X$^2$ represents a bivalent pyrazole residue and R represents phenyl or 6-membered heteroaryl which is optionally substituted as defined above.

Representative compounds in accordance with Formula II include those in which the moiety —X$^2$—R is selected from:

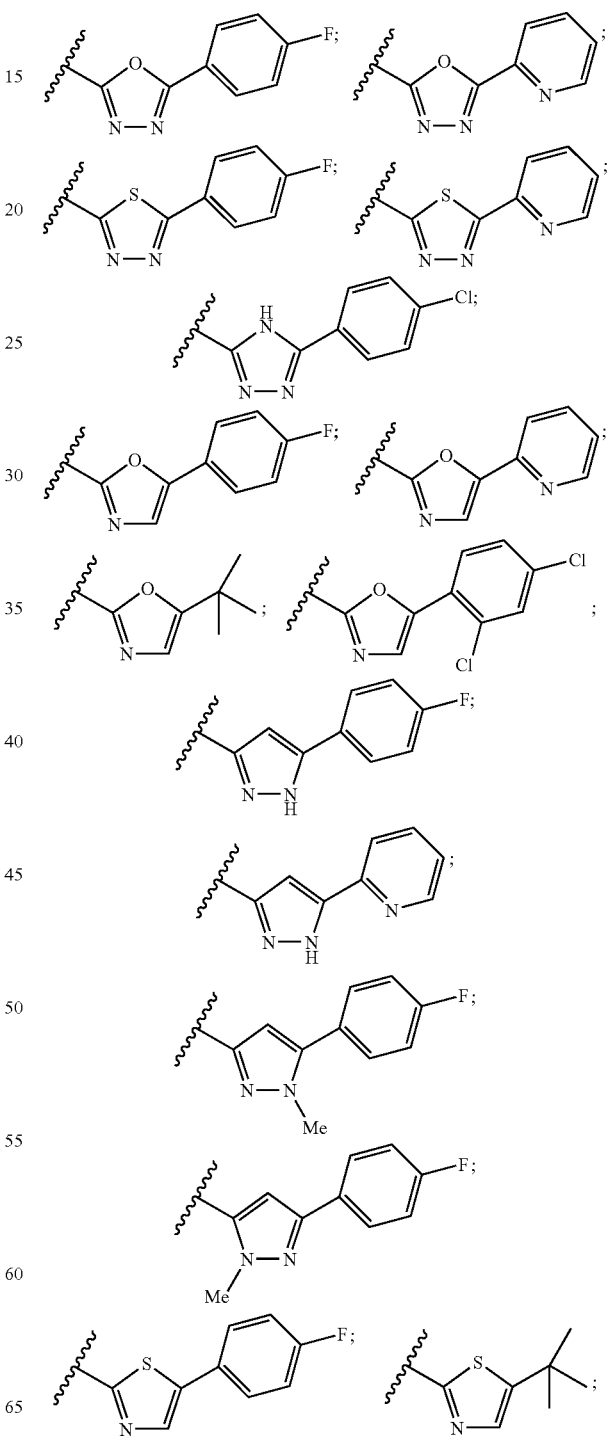

-continued

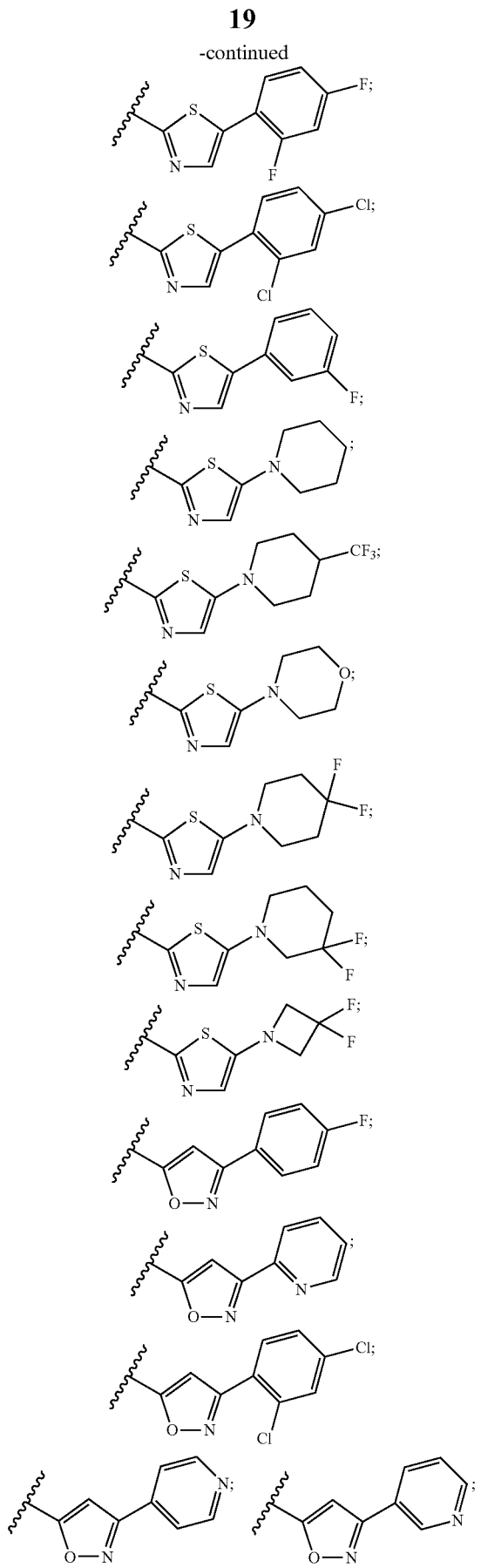

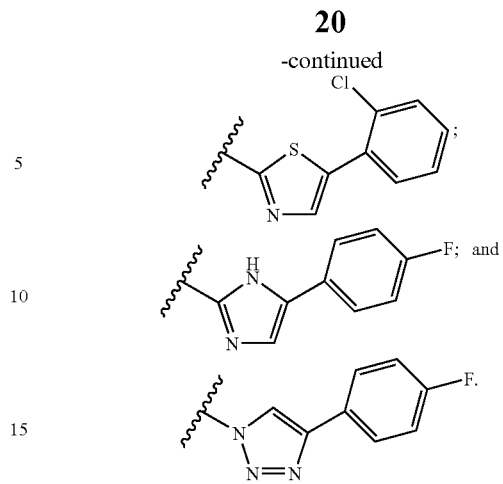

A preferred subclass of the compounds of Formula II are the 2-substituted-[6S,9R,11R]2',3',4',5,5',6,7,8,9,10-decahydro-5'-(2,2,2-trifluoroethyl)-spiro[6,9-methanobenzocyclooctene-11,3'-[1,2,5]thiadiazole]1',1'-dioxides of formula II(a):

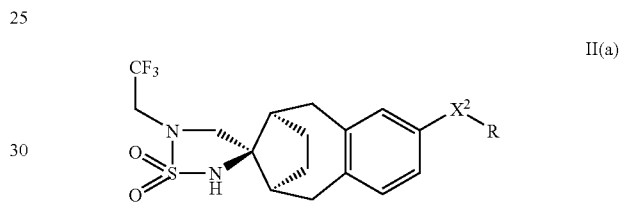

II(a)

wherein R and $X^2$ have the same meanings and preferred identities as before;

and pharmaceutically acceptable salts thereof.

Within this subclass, $X^2$ is very aptly 5-substituted-thiazol-2-yl, 5-substituted-4-methylthiazol-2-yl, 5-substituted-1-methylpyrazol-3-yl, 1-substituted-imidazol-4-yl or 1-substituted-1,2,4-triazol-3-yl.

Preferably, R represents optionally-substituted phenyl or heteroaryl as described previously, in particular 4-fluorophenyl, 4-chlorophenyl or 3,4-difluorophenyl.

Particularly preferred identities of R—$X^2$— include 5-(4-fluorophenyl)-1-methylpyrazol-3-yl and 1-(4-fluorophenyl) imidazol-4-yl.

The synthesis of these and other compounds of formula II is described in WO 03/093252, the contents of which are incorporated herein by reference.

A third preferred subset of the compounds of formula I are those defined by formula III:

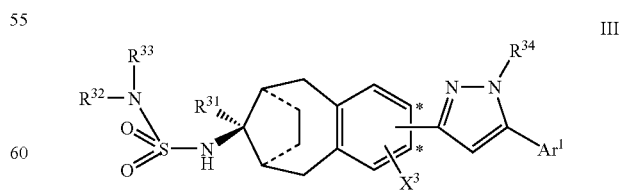

III wherein the pyrazole group is attached at one of the positions indicated by an asterisk and $X^3$ is attached at a position adjacent thereto;

$X^3$ represents H, OH, $C_{1-4}$alkoxy, Cl or F;

Ar¹ represents phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy;

$R^{34}$ represents a hydrocarbon group of 1-5 carbon atoms which is optionally substituted with up to 3 halogen atoms;

$R^{31}$ represents H or together with $R^{33}$ represents —$CH_2$—;

$R^{32}$ represents H or a hydrocarbon group of 1-10 carbon atoms which is optionally substituted with CN or $C_{1-4}$alkoxy or up to 5 fluorine atoms, or $R^{32}$ and $R^{33}$ together may complete a heterocyclic ring of up to 6 members which optionally bears up to 3 substituents independently selected from halogen, $CF_3$, $CHF_2$, $CH_2F$, $NO_2$, CN, $OCF_3$, $C_{1-6}$alkyl and $C_{1-6}$alkoxy;

$R^{33}$ represents H or $C_{1-4}$alkyl, or together with $R^{32}$ completes a heterocyclic ring as defined above, or together with $R^{31}$ represents —$CH_2$—;

and the pharmaceutically acceptable salts thereof.

It will be readily apparent to those skilled in the art that any compound in accordance with formula III may exist in two enantiomeric forms, depending on which of the ring positions indicated by an asterisk is bonded to the pyrazole ring. Formula III thus encompasses enantiomers of formulae IIIa and IIIb:

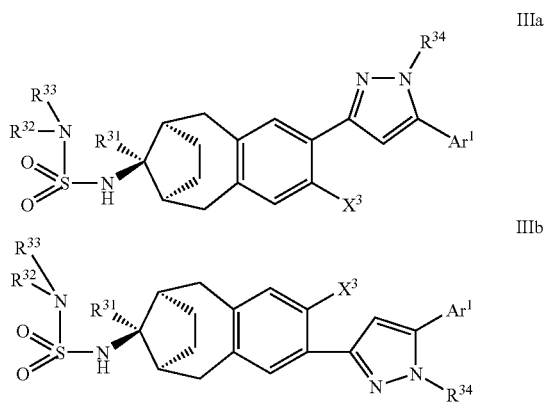

wherein $X^3$, Ar¹, $R^{31}$, $R^{32}$, $R^{33}$ and $R^{34}$ are as defined previously;

and also enantiomers of formulae IIIc and IIId:

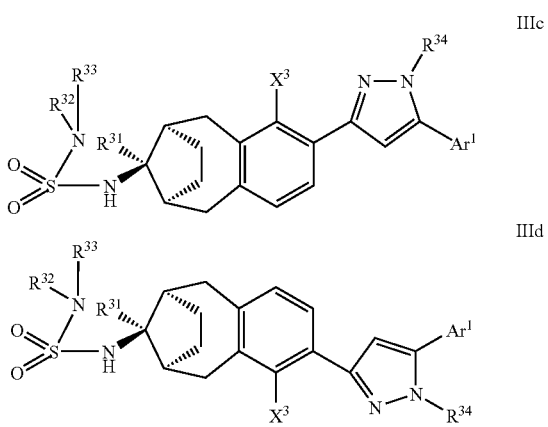

wherein $X^3$, Ar¹, $R^{31}$, $R^{32}$, $R^{33}$ and $R^{34}$ are as defined previously;

It will also be apparent that when $X^3$ represents H formula IIIa is identical to formula IIIc and formula IIIb is identical to formula IIId.

It is to be emphasised that the invention, for each compound in accordance with formula III, encompasses both enantiomeric forms, either as homochiral compounds or as mixtures of enantiomers in any proportion.

Preferably, the compound of formula III is a homochiral compound of formula IIIa or formula IIIc, or a pharmaceutically acceptable salt thereof.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits.

In the compounds of formula III, $X^3$ preferably represents H, OH or F, more preferably H or F. In one particular embodiment, $X^3$ is H. In another particular embodiment, $X^3$ is F. Preferably $X^3$ is H.

Ar¹ represents phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy. Examples of suitable 6-membered heteroaryl groups represented by Ar¹ include pyridyl, pyrazinyl, pyrimidinyl, pyridazinyl and triazinyl, of which pyridyl is a preferred example. Preferably, the phenyl or heteroaryl ring bears 0 to 2 substituents. Preferred substituents include halogen (especially chlorine and fluorine), CN, $C_{1-6}$alkyl (especially methyl), $C_{1-6}$alkoxy (especially methoxy), $OCF_3$ and $CF_3$. If two or more substituents are present, preferably not more than one of them is other than halogen or alkyl. Examples of groups represented by Ar¹ include phenyl, monohalophenyl, dihalophenyl, trihalophenyl, cyanophenyl, methylphenyl, methoxyphenyl, trifluoromethylphenyl, trifluoromethoxyphenyl, pyridyl, monohalopyridyl and trifluoromethylpyridyl, wherein "halo" refers to fluoro or chloro. Suitable specific values for Ar¹ include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 3,4,5-trifluorophenyl, 4-cyanophenyl, 4-methylphenyl, 4-methoxyphenyl, 2-(trifluoromethyl)phenyl, 4-(trifluoromethyl)phenyl, 4-(trifluoromethoxy)phenyl, pyridin-2-yl, pyridin-3-yl, pyridin-4-yl, pyrazin-2-yl, 5-methylpyridin-2-yl, 5-fluoropyridin-2-yl, 5-chloropyridin-2-yl, 5-(trifluoromethyl)pyridin-2-yl and 6-(trifluoromethyl)pyridin-3-yl. Preferred examples include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 4-(trifluoromethyl)phenyl, pyridin-2-yl, pyridin-3-yl and pyridin-4-yl.

In a particularly preferred embodiment, Ar¹ represents 4-fluorophenyl.

$R^{34}$ represents a hydrocarbon group of 1-5 carbon atoms which is optionally substituted with up to 3 halogen atoms, and thus may comprise cyclic or acyclic hydrocarbon residues or combinations thereof, saturated or unsaturated, up to a maximum of 5 carbon atoms in total. The hydrocarbon group represented by $R^{34}$ is preferably unsubstituted or is substituted with up to 3 fluorine atoms Examples include methyl, ethyl, n-propyl, isopropyl, n-butyl, sec-butyl, t-butyl, fluoromethyl, difluoromethyl, trifluoromethyl, 2,2,2-trifluoroethyl, cyclopropyl, cyclopropylmethyl and allyl. Preferred examples include methyl, ethyl and 2,2,2-trifluoroethyl. Most preferably, $R^{34}$ represents methyl.

$R^{32}$ represents H or a hydrocarbon group of 1-10 carbon atoms which is optionally substituted with CN, $C_{1-4}$alkoxy, or with up to 5 fluorine atoms. Preferred hydrocarbon groups represented by $R^{32}$ include alkyl, cycloalkyl, cycloalkylalkyl, alkenyl, alkynyl and benzyl groups optionally bearing up to 5, preferably up to 3 fluorine substituents. Said alkyl, cycloalkyl, cycloalkylalkyl, alkenyl and alkynyl groups typically comprise up to 6 carbon atoms. Examples of groups represented by $R^{32}$ include H, benzyl, n-propyl, 2,2-dimethylpropyl, n-butyl, isopropyl, t-butyl, 2,2,2-trifluoroethyl, 2,2-difluoroethyl, 2,2,3,3,3-pentafluoropropyl, 3,3,3-trifluoropropyl, 1-methyl-2,2,2-trifluoroethyl, cyanomethyl, 2-methoxyethyl, allyl, 2-methylprop-2-enyl, 2-fluoroprop-2-enyl, prop-2-ynyl, cyclopropyl, cyclobutyl and cyclopropylmethyl.

Alternatively, $R^{32}$ may combine with $R^{33}$ to complete a heterocyclic ring of up to 6 members which is optionally substituted as defined previously. Said ring preferably comprises at most one heteroatom selected from O, N and S in addition to the nitrogen to which $R^{32}$ and $R^{33}$ are mutually attached. Suitable rings include azetidinyl, pyrrolidinyl, piperidinyl, piperazinyl, morpholinyl and thiomorpholinyl. Preferred substituents include $CF_3$, halogen (especially chlorine or fluorine) and alkyl such as methyl. If two or more substituents are present, preferably not more than one of them is other than halogen or alkyl.

$R^{33}$ may alternatively represent H or $C_{1-4}$alkyl, such as methyl, or may together with $R^{31}$ represent $-CH_2-$. Preferably, $R^{33}$ represents H, or completes a ring with $R^{32}$, or together with $R^{31}$ represents $-CH_2-$.

Examples of compounds in accordance with formula III include compounds of formula IIIa or formula IIIc in which $Ar^1$ is 4-fluorophenyl, $R^{34}$ is methyl and $R^{31}$, $R^{32}$, $R^{33}$ and $X^3$ are as indicated in the following table:

| Formula (IIIa/IIIc) | $X^3$ | $R^{31}$ | $R^{33}$ | $R^{32}$ |
|---|---|---|---|---|
| IIIa | F | | $CH_2$ | 2,2,2-trifluoroethyl |
| IIIc | F | | $CH_2$ | 2,2,2-trifluoroethyl |
| IIIa | OH | | $CH_2$ | 2,2,2-trifluoroethyl |
| * | | H | $CH_2$ | allyl |
| * | | H | $CH_2$ | n-propyl |
| * | | H | $CH_2$ | 2,2-dimethylpropyl |
| * | | H | $CH_2$ | cyclobutyl |
| * | | H | $CH_2$ | benzyl |
| * | | H | $CH_2$ | n-butyl |
| * | | H | $CH_2$ | cyclopropylmethyl |
| * | | H | $CH_2$ | 3,3,3-trifluoropropyl |
| * | | H | $CH_2$ | isopropyl |
| * | | H | $CH_2$ | t-butyl |
| * | | H | $CH_2$ | cyclopropyl |
| * | | H | $CH_2$ | 2,2,3,3,3-pentafluoropropyl |
| * | | H | $CH_2$ | 2,2-difluoroethyl |
| * | | H | H | H | $CF_3CH_2$ |
| * | | H | H | | 4-$CF_3$-piperidin-1-yl |
| * | | H | H | H | n-propyl |
| * | | H | H | Me | n-propyl |
| * | | H | H | H | cyclobutyl |
| * | | H | H | Me | methyl |

*when $X^3$ is H, formulae IIIa and IIIc are identical.

The synthesis of compounds of formula III in which $R^{31}$ and $R^{33}$ together represent $-CH_2-$ is described in WO 2004/039800, the contents of which are incorporated herein by reference.

The synthesis of compounds of formula III in which $R^{31}$ represents H is described in WO 2004/039370, the contents of which are incorporated herein by reference.

Another preferred subset of the compounds of formula I are those defined by formula IV:

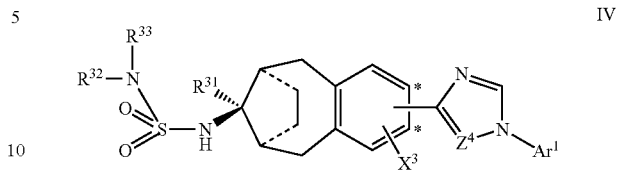

wherein $Z^4$ represents N or CH and the resulting imidazole or triazole group is attached at one of the positions indicated by an asterisk and $X^3$ is attached at a position adjacent thereto; and $X^3$, $Ar^1$, $R^{31}$, $R^{32}$ and $R^{33}$ have the same meanings and preferred identities as before;
and the pharmaceutically acceptable salts thereof.

It will be readily apparent to those skilled in the art that any compound in accordance with formula IV may exist in two enantiomeric forms, depending on which of the ring positions indicated by an asterisk is bonded to the imidazole or triazole ring. Formula IV thus encompasses enantiomers of formulae IVa and IVb:

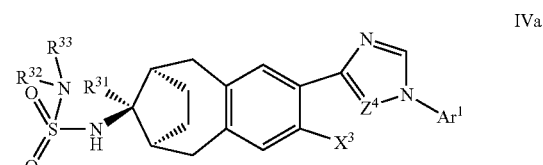

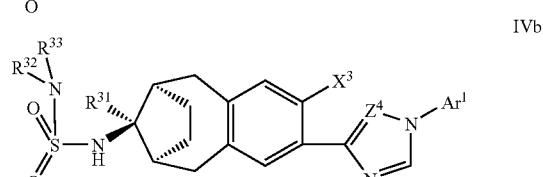

wherein $Z^4$, $X^3$, $Ar^1$, $R^{31}$, $R^{32}$, $R^{33}$ and $R^{34}$ are as defined previously;
and also enantiomers of formulae IIIc and IIId:

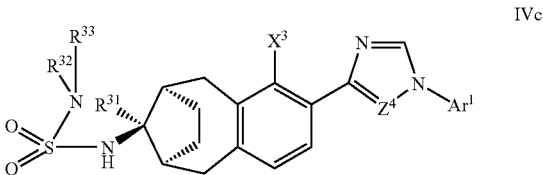

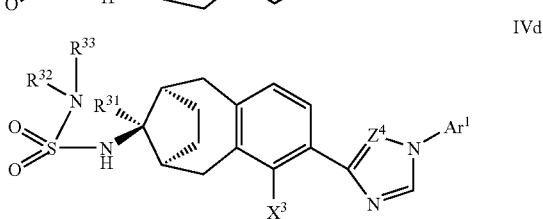

wherein $Z^4$, $X^3$, $Ar^1$, $R^{31}$, $R^{32}$, $R^{33}$ and $R^{34}$ are as defined previously;

It will also be apparent that when $X^3$ represents H formula IVa is identical to formula IVc and formula IVb is identical to formula IVd.

It is to be emphasised that the invention, for each compound in accordance with formula W, encompasses both enantiomeric forms, either as homochiral compounds or as mixtures of enantiomers in any proportion.

Preferably, the compound of formula IV is a homochiral compound of formula IVa or formula IVc, or a pharmaceutically acceptable salt thereof.

Specific examples of compounds in accordance with formula IV include the compounds of formula IVa in which $X^3$ is H, $Ar^1$ is 4-fluorophenyl, and $Z^4$, $R^{31}$, $R^{32}$ and $R^{33}$ are as indicated in the following table:

| $Z^4$ | $R^{31}$ | $R^{33}$ | $R^{32}$ |
|---|---|---|---|
| CH | H | H | n-propyl |
| CH | H | H | cyclobutyl |
| CH | H | | —$CH_2CH_2CH_2$— |
| CH | H | H | 2,2,2-trifluoroethyl |
| N | H | H | cyclobutyl |
| N | H | H | n-propyl |
| CH | $CH_2$ | | cyclobutyl |
| CH | $CH_2$ | | n-propyl |
| CH | $CH_2$ | | allyl |
| CH | $CH_2$ | | cyclopropyl |
| CH | $CH_2$ | | cyclopropylmethyl |
| CH | $CH_2$ | | 3,3,3-trifluoropropyl |
| CH | $CH_2$ | | isopropyl |
| CH | $CH_2$ | | 2-fluoroprop-2-enyl |
| CH | $CH_2$ | | prop-2-ynyl |
| CH | $CH_2$ | | 2-methylprop-2-enyl |
| CH | $CH_2$ | | H |
| CH | $CH_2$ | | cyanomethyl |
| N | $CH_2$ | | allyl |
| N | $CH_2$ | | cyclopropyl |
| N | $CH_2$ | | cyclobutyl |
| N | $CH_2$ | | n-propyl |
| N | $CH_2$ | | 2-methoxyethyl |
| CH | $CH_2$ | | 1-methyl-2,2,2-trifluoroethyl |

The synthesis of compounds of formula W is described in WO 2005/030731, the contents of which are incorporated herein by reference.

Compounds in accordance with formula I have been shown to inhibit the proteolytic action of gamma-secretase towards a number of protein substrates, including Notch and APP, both in vitro and in vivo. Preferred examples combine an extremely high activity towards the enzyme with favourable properties in terms of pharmacokinetics, pharmacodynamics, absorption, distribution, metabolism, and/or excretion, enabling therapeutically useful effects to be obtained without incurring unacceptable side effects.

In view of this desirable and unexpected activity profile, the compounds are suitable for use in treatment of conditions associated with Notch signalling, in particular cancer.

Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

Cancers that may be treated by the compounds, compositions and methods of the invention include, but are not limited to: breast, prostate, colon, lung, brain, testicular, stomach, pancreas, skin, small intestine, large intestine, throat, head and neck, oral, bone, liver, bladder, kidney, thyroid and blood.

Cancers that may be treated by the compounds, compositions and methods of the invention in particular include all types in which Notch signalling is known to play a role in the initial formation, proliferation or metastasis of cancerous cells. Modified Notch1 signalling has been implicated in lymphoblastic leukemia/lymphomas, mammary gland tumors, lung cancer, neuroblastomas, skin cancer, cervical cancer, epithelial tumors and prostate cancer. (Allenspach et. al., *Cancer Biology and Therapy*, 1:5, 466-476, 2002). Therefore compounds of the instant invention are useful in the treatment of the above described cancers.

Activating mutations in Notch1 are implicated in human T Cell Acute Lymphoblastic Leukemia (T-ALL) (Weng, et al., *Science*, 306:269-271 (2004). Compounds of the instant invention are therefore useful in the treatment of T-ALL.

Cancers that may be treated by the compounds, compositions and methods of the invention include: breast, prostate, colon, ovarian, colorectal, brain and lung.

Cancers that may be treated by the compounds, compositions and methods of the invention include: lymphoma and leukemia.

Cancers that may be treated by the compounds, compositions and methods of the invention include breast cancer.

Cancers that may be treated by the compounds, compositions and methods of the invention include lung cancer, in particular non-small cell lung cancer.

Cancers that may be treated by the compounds, compositions and methods of the invention include colon cancer and colorectal cancer.

Cancers that may be treated by the compounds, compositions and methods of the invention include brain cancer, including glioma, medulloblastoma and ependymoma.

Cancers that may be treated by the compounds, compositions and methods of the invention include familial adenomatous polyposis (FAP).

Cancers that may be treated by the compounds, compositions and methods of the invention include Barrett's esophagus.

Exposure to compounds of the instant invention has been shown to cause cell cycle arrest, in particular $G_0/G_1$ arrest, in populations of cells with a high level of Notch expression, but not in populations lacking such expression. Furthermore, it has been found that the arrested cells selectively undergo apoptosis. Hence, the compounds of the instant invention have the potential to selectively target malignant cells without damaging neighbouring healthy cells.

The compounds of the instant invention are suitable for treating cancer via the selective targeting of cancer stem cells.

The compounds of formula I may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds for the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. For example, compounds of the instant invention can be administered in a total daily dose of up to 1000 mg. Compounds of the instant invention can be administered once daily (QD), or divided into multiple daily doses such as twice daily (BID), and three times daily (TID). Compounds of the instant invention can be administered at a total daily dosage of up to 1000 mg, e.g., 200 mg, 300 mg, 400 mg, 600 mg, 800 mg or 1000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

In a further example of intermittent dosing, the compounds of the instant invention are administered on three consecutive days followed by four days of rest.

In a yet further example of intermittent dosing, the compounds of the instant invention are administered on one day, followed by six days of rest.

In a yet further example of intermittent dosing, the compounds of the instant invention are administered on one day, followed by 10 to 13 days of rest.

The instant compounds are also useful in combination with known therapeutic agents and anti-cancer agents. For example, instant compounds are useful in combination with known anti-cancer agents.

Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxel, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydrOxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in WO 03/13526.

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J Cardiovasc. Pharmacol.* 1998; 31:909-913; *J. Biol. Chem.* 1999; 274: 9116-9121; *Invest. Opthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid WO 01/60807, and 2(R)-7-(3-(2-chloro-4-(4-fluorophenoxy)phenoxy)propoxy)-2-ethylchromane-2-carboxylic acid WO 02/026729.

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8): 1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, $5HT_3$ receptor antagonists, such as ondansetron, granisetron, tropisetron, and zatisetron, $GABA_B$ receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a $5HT_3$ receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfmavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with other γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039600, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/

031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with one or more of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); and zoledronate (Zometa®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HW protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, a γ-secretase and/or NOTCH inhibitor, an agent that interferes with receptor tyrosine kinases (RTKs), an agent that interferes with a cell cycle checkpoint, and any of the therapeutic agents listed above.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HW protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, a γ-secretase and/or NOTCH inhibitor, an agent that interferes with receptor tyrosine kinases (RTKs), an agent that interferes with a cell cycle checkpoint, and any of the therapeutic agents listed above.

Yet another embodiment of the invention is a method of treating cancer that comprises administering to a patient in need thereof a therapeutically effective amount of a compound of formula I or a pharmaceutically acceptable salt thereof in combination with a second medicament selected from: paclitaxel (Taxol®, optionally in combination with carboplatin); docetaxel (Taxotere®); trastuzumab (Herceptin®); tamoxifen (Nolvadex®); bevacuzimab (Avastin®); and erlotinib (Tarceva®).

The invention further encompasses a method of treating or preventing cancer that comprises administering to a patient in need thereof a therapeutically effective amount of a compound of formula I or a pharmaceutically acceptable salt thereof in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, a γ-secretase and/or NOTCH inhibitor, an agent that interfere with receptor tyrosine kinases (RTKs), an agent that interferes with a cell cycle checkpoint, and any of the therapeutic agents listed above.

Any of the specific dosages and dosage schedules applicable to the compounds of the instant invention may also be applicable to the therapeutic agents to be used in a combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally or intravenously. However, it is also within the scope of the present invention to administer a compound of the instant invention by one mode of administration, e.g. orally, and to administer the second therapeutic agent by another mode of administration, e.g. intravenously or by any of the other administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The term "administration" and variants thereof (e.g., "administering") in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating cancer" and "treatment of cancer" encompass prophylactic treatments as well as treatments targeting an existing cancerous condition. Thus, the compounds of the instant invention may be administered to a patient alone or in combination with one or more conventional chemotherapeutic, radiotherapeutic or surgical interventions, for the purpose of arresting or attenuating an existing malignant condition by killing cancerous cells. However, said compounds may also be administered simultaneously with or subsequent to a conventional chemotherapeutic, radiotherapeutic or surgical intervention for the purpose of preventing or delaying the recurrence or metastasis of cancerous cells.

All patents, publications and pending patent applications identified are hereby incorporated by reference.

Suitable methods of assaying the level of activity of compounds of the present invention towards γ-secretase are disclosed in WO 01/70677, WO 03/093252, and in *Biochemistry*, 2000, 39(30), 8698-8704 (APP as substrate); and in *Biochemistry* (2003), 42, 7580-7586 (Notch as substrate).

The above-identified individual compounds in accordance with formulae I, II, III and W all had an $ED_{50}$ of less than 1 µM, typically less than 0.1 µM and in preferred cases less than 10 nM in the above-referenced assays.

Assay for Cell Cycle Arrest

Cells expressing Notch (ALL-SIL, DND-41, HPB-ALL or TALL-1) (Weng et al, *Science*, 306 (2004), 269-71) were incubated in the presence or absence of a compound of the instant invention (e.g. the compound of formula II(a) above in which R—$X^2$ represents 5-(4-fluorophenyl)-1-methylpyrazol-3-yl—see WO 03/093252 example 14) at concentrations up to 10 µM. At the end of the incubation (typically 4-8 days), the cells were collected, fixed in 70% ethanol on ice for >2 hours, washed, then labelled for 15 min at 37° C. with propidium iodide (0.2 mg/ml) (PI) in the presence of 0.1% Triton $X^{100}$ and 0.2 mg/ml RNase and subjected to FACS analysis. In comparison to untreated controls, treated cell cultures showed severe loss of $G_2$- and S-phase populations, consistent with $G_0/G_1$ arrest.

Similar results were obtained using the compound in accordance with embodiment (A) described earlier herein, in which $R^2$ represents H, $R^{14}$ represents 2,2,2-trifluoroethyl, $R^4$ represents —CH=CHCH$_2$N(R$^{16}$)$_2$, and —N(R$^{16}$)$_2$ represents 4-trifluoromethylpiperidin-1-yl (example 75 of WO 02/36555).

Assay for Apoptosis

This assay relies on the detection of phosphatidylserine (PS) on the external surface of apoptotic cells via binding to Annexin V, since PS in intact cells remains inaccessible. The bound Annexin V is labelled with FITC-conjugated antibody for analysis by FACS. Kits for carrying out this assay are available commercially (e.g. from BD cat. no. 556547).

Cells were incubated as described above in the presence of Annexin V, then collected, washed, labelled with FITC-Annexin V and PI antibodies, and analysed by FACS. Due to exposure of PS-bound Annexin V on the outside of apoptotic, but not normal, cells, FACS technologies enables quantification of the population of apoptotic cells highly stained by FITC-conjugated antibodies raised against Annexin V.

Typically, cells treated with 0.1% DMSO for 7 days showed negligible accessible expression of Annexin V, the bulk of the cell population remaining unstained. In contrast, exposure to compounds of the instant invention at 10 μM or 1.0 μM for 7 days (replenished twice during the experiment) lead to a reduction of the number of such cells with low accessibility of Annexin V, and the appearance of a highly labelled population of cells, consistent with known redistribution of this protein during apoptosis. Subsequent experiments failed to show equivalent apoptosis when the duration of treatment (4 days) was insufficient to cause cell cycle arrest, or the concentration of inhibitor was insufficient to cause arrest, or when a Notch-independent cell line was used. Furthermore, a titration comparison of representative inhibitors in HPB-ALL cells over 6 days revealed a perfect correlation between the treatments that caused apoptosis and those that caused parallel cell cycle arrest.

Assay for Cell Viability

Cell lines such as ALL-SIL, DND-41, HPB-ALL, and T-ALL-1 cell lines are seeded to 96 well plates (1×10$^4$ cells in 90 μl/well) in media specified by the cell line supplier (DSMZ, German National Resource Centre for Biological Material). Following overnight incubation of 90 μl at 37° C. in 5% CO$_2$, 10 μl of media containing 10× γ-secretase inhibitor stock is added, yielding a final concentration of 0.1% DMSO. Media containing inhibitor (75 μl) is replaced after a brief centrifugation every 2 days and the cells are completely resuspended. Cell viability is measured following 8 days of treatment using ATPlite (PerkinElmer), according to the manufacturer's instructions.

Assay to Measure Gamma-Secretase Inhibition by Monitoring Cleavage of the Substrate Notch 1

Treated cells are lysed in buffer containing 1% Triton X-100, 0.5% NP-40, 0.2% SDS in TBS and vortexed. Samples are rocked for 25 minutes at 4° C., sonicated for 15 seconds and centrifuged at 14,000×g to collect supernatant. Protein is quantitated using the Biorad DC Protein assay (#500-0116) and 30-50 μg of protein separated on 10-20% Tricine gel. Proteins are transferred to nitrocellulose membranes, blocked in 10% Milk for 1 hour, and probed with cleaved Notch 1 antibody (#2421, Cell Signaling Technologies) diluted 1:1000 in PBS overnight at 4° C. Membranes washed in PBS are subsequently probed with anti-rabbit-HRP at 1:7000 for 1 h and proteins revealed to film using Pierce SuperSignal West Femto.

Assay to Measure Inhibition of the Notch Pathway by Monitoring Notch Target Genes Response in Cells or Tumors RNA is extracted according to the RNeasy kit from Qiagen and cDNA prepared as described by Applied Biosystems using the High Capacity cDNA Archive kit. Notch pathway response genes such as Hes1 and Hes5 are quantitated using Taqman Real-Time PCR with probes purchased from Applied Biosystems.

Assay for Anti-Tumor Activity

CD1 nude mice predosed with cyclophosphamide (100 mg/kg, i.p. for 3 days) are injected subcutaneously with 5×10$^6$ T-ALL-1 cells per mouse in PBS/matrigel. Tumor volume is monitored with calipers and when this reaches ~250 mm$^3$ the mice are dosed orally 4 days-On, 4-days-Off for a period of 24-32 days using inhibitor formulated in 0.5% methylcellulose. Body weight and tumor volume are recorded daily and all procedures are conducted according to IACUC guidelines.

The invention claimed is:

1. A method of treating a cancer associated with modified Notch signaling in a mammal comprising administering to said mammal a therapeutically effective amount of a compound of formula I:

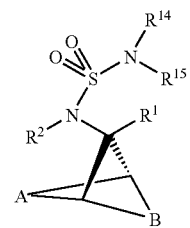

wherein:
A is

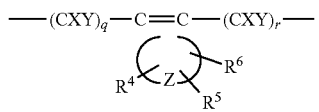

and B is selected from —(CXY)$_p$—; —(CXY)$_q$CY=CY(CXY)$_r$—; —(CXY)$_x$NR$^{13}$(CXY)$_y$—;

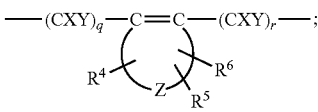

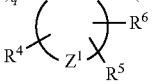; and

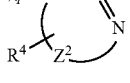

X represents halogen, R$^9$, —OR$^9$, —SR$^9$, —S(O)$_t$R$^{10}$ where t is 1 or 2, —OSO$_2$R$^9$, —N(R$^9$)$_2$, —COR$^9$, —CO$_2$R$^9$, —OCOR$^{10}$, —OCO$_2$R$^{10}$, —CON(R$^9$)$_2$, —SO$_2$N(R$^9$)$_2$, —OSO$_2$N(R$^9$)$_2$, —NR$^9$COR$^{10}$, —NR$^9$CO$_2$R$^{10}$ or —NR$^9$SO$_2$R$^{10}$;

Y represents H or C$_{1-6}$alkyl;

or X and Y together represent =O, =S, =N—OR$^{11}$ or =CHR$^{11}$;

provided neither A nor B comprises more than one —CXY— moiety which is other than —CH$_2$—;

Z completes an aromatic ring system of 5 to 10 atoms, of which 0 to 3 are selected from nitrogen, oxygen and sulfur and the remainder are carbon, or Z completes a non-aromatic ring system of 5 to 10 atoms, of which 0 to 3 are independently selected from oxygen, nitrogen and sulphur and the remainder are carbon;

Z$^1$ completes a non-aromatic ring system of 5 to 10 atoms, of which 0 to 3 are independently selected from oxygen, nitrogen and sulphur and the remainder are carbon;

Z$^2$ completes a 5- or 6-membered heteroaryl ring;

p is an integer from 1-6;

q and r are independently 0, 1 or 2;

x and y are independently 0, 1 or 2;

provided that at least one of A and B comprises a chain of 2 or more atoms, such that the ring completed by A and B contains at least 5 atoms;

R$^1$ represents H, C$_{1-4}$ alkyl, or C$_{2-4}$alkenyl, or R$^1$ and R$^{15}$ together may complete a 5-, 6- or 7-membered cyclic sulfamide;

R$^2$ represents H, C$_{1-6}$alkyl, C$_{6-10}$aryl, C$_{6-10}$arylC$_{1-6}$alkyl, C$_{3-6}$cycloalkyl or C$_{2-6}$acyl which is optionally substituted with a carboxylic acid group or with an amino group;

R$^4$, R$^5$ and R$^6$ independently represent R$^9$, halogen, CN, NO$_2$, —OR$^9$, —SR$^9$, —S(O)$_t$R$^{10}$ where t is 1 or 2, —N(R$^9$)$_2$, —COR$^9$, —CO$_2$R$^9$, —OCOR$^{10}$, —CH=N—OR$^{11}$, —CON(R$^9$)$_2$, —SO$_2$N(R$^9$)$_2$, —NR$^9$COR$^{10}$, —NR$^9$CO$_2$R$^{10}$, —NR$^9$SO$_2$R$^{10}$, —CH=CHCH$_2$N(R$^{16}$)$_2$, —CH$_2$OR$^{10}$, —CH$_2$N(R$^{16}$)$_2$, —NHCOCH$_2$OR$^{10}$ or —NHCOCH$_2$N(R$^{16}$)$_2$;

R$^7$ represents H or R$^8$; or two R$^7$ groups together with a nitrogen atom to which they are mutually attached may complete a pyrrolidine, piperidine, piperazine or morpholine ring;

R$^8$ represents C$_{1-10}$alkyl, perfluoroC$_{1-6}$alkyl, C$_{3-10}$cycloalkyl, C$_{3-6}$cycloalkylC$_{1-6}$alkyl, C$_{2-10}$alkenyl, C$_{2-10}$alkynyl, Ar or —C$_{1-6}$alkylAr;

R$^9$ represents H or R$^{10}$; or two R$^9$ groups together with a nitrogen atom to which they are mutually attached may complete a pyrrolidine, piperidine, piperazine or morpholine ring which is optionally substituted by R$^{12}$, —COR$^{12}$ or —SO$_2$R$^{12}$;

R$^{10}$ represents C$_{1-10}$alkyl, perfluoroC$_{1-6}$alkyl, C$_{3-10}$cycloalkyl, C$_{3-6}$cycloalkylC$_{1-6}$alkyl, C$_{2-10}$alkenyl, C$_{2-10}$alkynyl, C$_{6-10}$aryl, heteroaryl, heterocyclyl, C$_{6-10}$arylC$_{1-6}$alkyl, heteroarylC$_{1-6}$alkyl, heterocyclylC$_{1-6}$alkyl, C$_{6-10}$arylC$_{2-6}$alkenyl, or heteroarylC$_{2-6}$alkenyl, wherein the alkyl, cycloalkyl, alkenyl and alkynyl groups optionally bear one substituent selected from halogen, CF$_3$, NO$_2$, CN, —OR$^{11}$, —SR$^{11}$, —SO$_2$R$^{12}$, —COR$^{11}$, —CO$_2$R$^{11}$, —CON(R$^{11}$)$_2$, —OCOR$^{12}$, —N(R$^{11}$)$_2$ and —NR$^{11}$COR$^{12}$; and the aryl, heteroaryl and heterocyclic groups optionally bear up to 3 substituents independently selected from halogen, NO$_2$, CN, R$^{12}$, —OR$^{11}$, —SR$^{11}$, —SO$_2$R$^{12}$, —COR$^{11}$, —CO$_2$R$^{11}$, —CON(R$^{11}$)$_2$, —OCOR$^{12}$, —N(R$^{11}$)$_2$ and —NR$^{11}$COR$^{12}$;

R$^{11}$ represents H or R$^{12}$; or two R$^{11}$ groups together with a nitrogen atom to which they are mutually attached may complete a heterocyclic ring system of 3-10 atoms, 0-2 of which (in addition to said nitrogen atom) are selected from O, N and S, said ring system bearing 0-2 substituents selected from halogen, CN, NO$_2$, oxo, R$^{12}$, OH, OR$^{12}$, NH$_2$, NHR$^{12}$, CHO, CO$_2$H, COR$^{12}$ and CO$_2$R$^{12}$;

R$^{12}$ represents C$_{1-6}$alkyl which is optionally substituted with halogen, CN, OH, C$_{1-4}$alkoxy or C$_{1-4}$alkoxycarbonyl; perfluoroC$_{1-6}$alkyl, C$_{3-7}$cycloalkyl, C$_{2-6}$alkenyl, C$_{2-6}$alkynyl, Ar, —C$_{1-6}$alkylAr, ArOC$_{1-6}$alkyl or C-heterocyclyl which is optionally substituted with halogen, CN, C$_{1-6}$alkyl, OH, perfluoroC$_{1-6}$alkyl, C$_{2-6}$acyl, C$_{1-4}$alkoxy or C$_{1-4}$alkoxycarbonyl;

R$^{13}$ represents R$^9$, —COR$^{10}$, —CO$_2$R$^{10}$, —SO$_2$R$^{10}$, —CON(R$^9$)$_2$ or —SO$_2$N(R$^9$)$_2$;

R$^{14}$ represents H, C$_{1-10}$alkyl, perfluoroC$_{1-6}$alkyl, C$_{3-10}$cycloalkyl, C$_{3-6}$cycloalkylC$_{1-6}$alkyl, C$_{2-10}$alkenyl, C$_{2-10}$alkynyl, C$_{6-10}$aryl, heteroaryl, C$_{6-10}$arylC$_{1-6}$alkyl, or heteroarylC$_{1-6}$alkyl, wherein the alkyl, cycloalkyl, alkenyl and alkynyl groups optionally bear one substituent selected from halogen, CN, NO$_2$, —OR$^7$, —S(O)$_t$R$^8$ where t is 1 or 2, —N(R$^7$)$_2$, —COR$^7$, —CO$_2$R$^7$, —OCOR$^8$, —CON(R$^7$)$_2$, —NR$^7$COR$^8$, —C$_{1-6}$alkylNR$^7$COR$^8$, —NR$^7$CO$_2$R$^8$ and —NR$^7$SO$_2$R$^8$, and the aryl and heteroaryl groups optionally bear up to 3 substituents selected from R$^8$, halogen, CN, NO$_2$, —OR$^7$, —SR$^7$, —S(O)$_t$R$^8$ where t is 1 or 2, —N(R$^7$)$_2$, —COR$^7$, —CO$_2$R$^7$, —OCOR$^8$, —CON(R$^7$)$_2$, —NR$^7$COR$^8$, —C$_{1-6}$alkylNR$^7$COR$^8$, —NR$^7$CO$_2$R$^8$ and —NR$^7$SO$_2$R$^8$;

R$^{15}$ represents H or C$_{1-6}$alkyl; or R$^{15}$ and R$^1$ together complete a 5-, 6- or 7-membered cyclic sulfamide;

each R$^{16}$ independently represents H or R$^{10}$, or two R$^{16}$ groups together with the nitrogen to which they are mutually attached complete a mono- or bicyclic heterocyclic ring system of 5-10 ring atoms selected from C, N, O and S, said ring system optionally having an additional aryl or heteroaryl ring fused thereto, said heterocyclic system and optional fused ring bearing 0-3 substituents independently selected from halogen, oxo, NO$_2$, CN, R$^{12}$, —OR$^{11}$, —SR$^{11}$, —SO$_2$R$^{12}$, —COR$^{11}$, —CO$_2$R$^{11}$, —CON(R$^{11}$)$_2$, —OCOR$^{12}$, —N(R$^{11}$)$_2$ and —NR$^{11}$COR$^{12}$;

Ar represents phenyl or heteroaryl either of which optionally bears up to 3 substituents independently selected from halogen, CF$_3$, NO$_2$, CN, OCF$_3$, C$_{1-6}$alkyl and C$_{1-6}$alkoxy;

"heterocyclyl" at every occurrence thereof means a cyclic or polycyclic system of up to 10 ring atoms selected from C, N, O and S, wherein none of the constituent rings is aromatic and wherein at least one ring atom is other than C; and "heteroaryl" at every occurrence thereof means a cyclic or polycyclic system of up to 10 ring atoms selected from C, N, O and S, wherein at least one of the constituent rings is aromatic and wherein at least one ring atom is other than C;

or a pharmaceutically acceptable salt thereof.

2. The method according to claim 1, wherein said compound is a compound of formula IC:

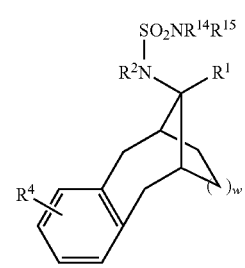

or a pharmaceutically acceptable salt thereof, wherein w is 1 or 2, and $R^1$, $R^2$, $R^4$, $R^{14}$ and $R^{15}$ are as defined in claim 1.

3. The method according to claim 2, wherein said compound is a compound of formula (A):

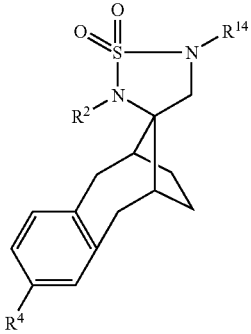

(A)

or a pharmaceutically acceptable salt thereof.

4. The method according to claim 3, wherein said compound is in accordance with formula II(a):

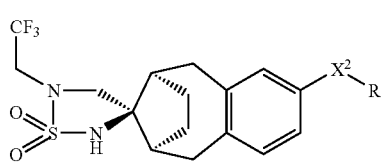

II(a)

wherein:
$X^2$ is a bivalent pyrazole, imidazole, triazole, oxazole, isoxazole, thiazole, isothiazole, thiadiazole or 1,3,4-oxadiazole residue optionally bearing a hydrocarbon substituent comprising 1-5 carbon atoms which is optionally substituted with up to 3 halogen atoms; and
R is selected from:
(i) $CF_3$ or an alkyl group of up to 6 carbon atoms, optionally substituted with halogen, $CF_3$, $CHF_2$, CN, OH, $CO_2H$, $C_{2-6}$acyl, $C_{1-4}$alkoxy or $C_{1-4}$alkoxycarbonyl;
(ii) a non-aromatic heterocyclic group comprising up to 7 ring atoms of which up to 3 are chosen from N, O and S and the remainder are carbon, bearing 0-3 substituents independently selected from oxo, halogen, CN, $C_{1-6}$alkyl, OH, $CF_3$, $CHF_2$, $CH_2F$, $C_{2-6}$acyl, $CO_2H$, $C_{1-4}$alkoxy and $C_{1-4}$alkoxycarbonyl;
(iii) phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy; and
(iv) $N(R^a)_2$ where each $R^a$ independently represents H or $C_{1-6}$alkyl which is optionally substituted with halogen, $CF_3$, $CHF_2$, CN, OH, $C_{1-4}$alkoxy or $C_{1-4}$alkoxycarbonyl;
or a pharmaceutically acceptable salt thereof.

5. The method according to claim 4, wherein $X^2$ represents 5-substituted-thiazol-2-yl, 5-substituted-4-methylthiazol-2-yl, 5-substituted-1-methylpyrazol-3-yl, 1-substituted-imidazol-4-yl or 1-substituted-1,2,4-triazol-3-yl; and R represents optionally-substituted phenyl or heteroaryl as described previously, in particular 4-fluorophenyl, 4-chlorophenyl or 3,4-difluorophenyl.

6. The method according to claim 1, wherein said compound is a compound of formula IVa:

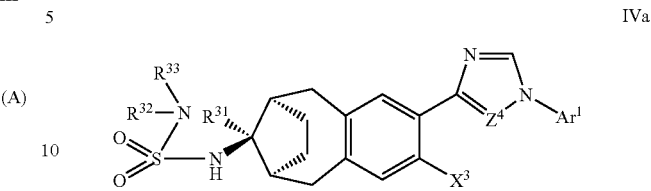

IVa wherein:
$Z^4$ represents CH or N;
$X^3$ represents H, OH, $C_{1-4}$alkoxy, Cl or F;
$Ar^1$ represents phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy;
$R^{31}$ represents H or together with $R^{33}$ represents —$CH_2$—;
$R^{32}$ represents H or a hydrocarbon group of 1-10 carbon atoms which is optionally substituted with CN or $C_{1-4}$alkoxy or up to 5 fluorine atoms, or $R^{32}$ and $R^{33}$ together may complete a heterocyclic ring of up to 6 members which optionally bears up to 3 substituents independently selected from halogen, $CF_3$, $CHF_2$, $CH_2F$, $NO_2$, CN, $OCF_3$, $C_{1-6}$alkyl and $C_{1-6}$alkoxy; and
$R^{33}$ represents H or $C_{1-4}$alkyl, or together with $R^{32}$ completes a heterocyclic ring as defined above, or together with $R^{31}$ represents —$CH_2$—;
or a pharmaceutically acceptable salt thereof.

7. The method according to claim 1, wherein the cancer is selected from breast, prostate, colon, ovarian, colorectal and lung cancers.

8. The method according to claim 1, wherein the cancer is lymphoma or leukemia.

9. The method according to claim 8, wherein the cancer is T-ALL.

10. The method according to claim 1, wherein the compound of formula I is administered in combination with another anti-cancer agent or therapeutic agent, optionally in conjunction with radiation therapy.

11. The method according to claim 10, wherein said other anti-cancer agent or therapeutic agent is selected from the group consisting of: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, a γ-secretase and/or NOTCH inhibitor, an agent that interferes with receptor tyrosine kinases (RTKs), and an agent that interferes with a cell cycle checkpoint.

12. The method of claim 4, wherein $X^2$—R is 5-(4-fluorophenyl)-1-methylpyrazol-3-yl, or an enantiomer thereof.

13. The method of claim 4, wherein $X^2$—R is
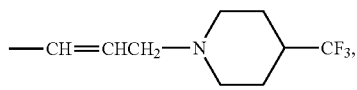
or an enantiomer thereof.
14. The method of claim 3, wherein the compound is
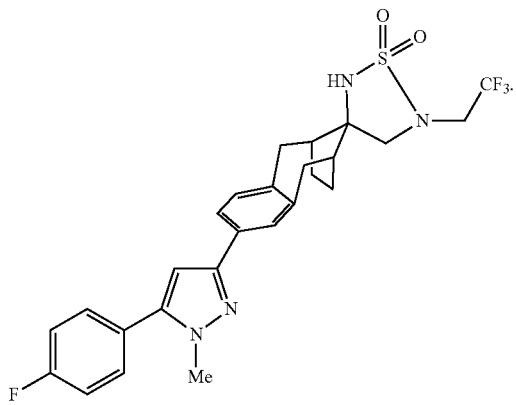
15. The method of claim 3, wherein the compound is
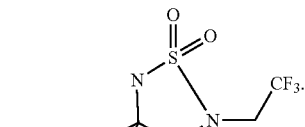
* * * * *